US010943689B1

(12) United States Patent
Holmes et al.

(10) Patent No.: US 10,943,689 B1
(45) Date of Patent: Mar. 9, 2021

(54) SYSTEMS AND METHODS FOR LABORATORY TESTING AND RESULT MANAGEMENT

(71) Applicant: Theranos, Inc., Palo Alto, CA (US)

(72) Inventors: Elizabeth A. Holmes, Palo Alto, CA (US); Sunny Balwani, Palo Alto, CA (US)

(73) Assignee: Labrador Diagnostics LLC, Wilmington, DE (US)

(*) Notice: Subject to any disclaimer, the term of this patent is extended or adjusted under 35 U.S.C. 154(b) by 872 days.

(21) Appl. No.: 14/736,259

(22) Filed: Jun. 10, 2015

Related U.S. Application Data

(63) Continuation-in-part of application No. 14/480,600, filed on Sep. 8, 2014, now abandoned, which is a continuation-in-part of application No. 14/020,785, filed on Sep. 6, 2013, now abandoned.

(60) Provisional application No. 61/874,983, filed on Sep. 6, 2013, provisional application No. 62/010,421, filed on Jun. 10, 2014.

(51) Int. Cl.
G16H 40/20 (2018.01)
G06Q 30/06 (2012.01)
G06Q 50/22 (2018.01)
H04N 5/232 (2006.01)

(52) U.S. Cl.
CPC ......... G16H 40/20 (2018.01); G06Q 30/0633 (2013.01); G06Q 50/22 (2013.01); H04N 5/23206 (2013.01); H04N 5/23216 (2013.01)

(58) Field of Classification Search
CPC .. G06F 19/327; G06Q 50/22; G06Q 30/0633; G16H 40/20; H04N 5/23216; H04N 5/23206
See application file for complete search history.

(56) References Cited

U.S. PATENT DOCUMENTS

| 5,675,760 | A | 10/1997 | Houwen et al. |
| 7,291,497 | B2 | 11/2007 | Holmes et al. |
| 8,374,886 | B2 | 2/2013 | Friedman et al. |
| 8,615,413 | B2 | 12/2013 | McKee et al. |
| 8,670,996 | B1 | 3/2014 | Weiss |
| 2005/0234741 | A1 | 10/2005 | Rana et al. |
| 2007/0094044 | A1 | 4/2007 | Stone et al. |
| 2007/0168382 | A1 | 7/2007 | Tillberg et al. |
| 2009/0088336 | A1 | 4/2009 | Burd et al. |

(Continued)

FOREIGN PATENT DOCUMENTS

| WO | WO-2010054284 A1 * | 5/2010 | ............. G16B 45/00 |
| WO | 2014127379 A1 | 8/2014 | |
| WO | 2015035309 A1 | 3/2015 | |

OTHER PUBLICATIONS

Pathology; Introducing LabNexusTM Cloud-Based Lab Connectivity, Mar. 1, 2012, Computers, Networks &Communications via NewsRx.com. (Year: 2012).*

(Continued)

Primary Examiner — Christopher L Gilligan

(57) ABSTRACT

In one embodiment, a method is provided comprising displaying a laboratory test menu on a mobile computing device, where the test menu is variable-based on geographic location; selecting one or more tests from said test menu; and using the mobile computing device to send a laboratory test request to a server.

17 Claims, 13 Drawing Sheets

(56) References Cited

U.S. PATENT DOCUMENTS

| | | | |
|---|---|---|---|
| 2010/0318379 A1* | 12/2010 | Demopulos | G06Q 10/10 |
| | | | 705/3 |
| 2011/0258170 A1 | 10/2011 | Duggan et al. | |
| 2011/0271177 A1* | 11/2011 | Bastos dos Santos | ...... |
| | | | G06F 40/174 |
| | | | 715/256 |
| 2012/0300265 A1* | 11/2012 | Seo | G06K 9/3275 |
| | | | 358/448 |
| 2013/0079236 A1 | 3/2013 | Holmes | |
| 2013/0103413 A1 | 4/2013 | Meralli | |
| 2013/0115685 A1 | 5/2013 | Holmes et al. | |
| 2013/0131994 A1* | 5/2013 | Birdwell | G06F 19/22 |
| | | | 702/19 |
| 2013/0166315 A1* | 6/2013 | Fonseca | G06F 19/366 |
| | | | 705/2 |
| 2013/0226605 A1 | 8/2013 | Miller et al. | |
| 2015/0073815 A1 | 3/2015 | Holmes et al. | |

OTHER PUBLICATIONS

Office Action dated Apr. 24, 2015 for U.S. Appl. No. 14/020,785.
Office Action dated Jan. 27, 2017 for U.S. Appl. No. 14/480,600.
Office Action dated Nov. 2, 2017 for U.S. Appl. No. 14/480,600.

\* cited by examiner

SYSTEMS AND METHODS FOR LABORATORY TESTING AND RESULT MANAGEMENT

CROSS-REFERENCE TO RELATED APPLICATION

This application claims priority to U.S. Patent Application Ser. No. 62/010,421 filed Jun. 10, 2014 and to U.S. patent application Ser. No. 14/480,600 filed Sep. 8, 2014 which claims priority to U.S. Provisional Application Ser. No. 61/874,983 filed Sep. 6, 2013. All of the foregoing are fully incorporated herein by reference for all purposes.

BACKGROUND

Laboratory testing of blood samples from patients has traditionally been based on a physical, paper laboratory test request that a patient receives from a doctor. That physical document is usually then physically delivered by the patient to a technician or administrator at a laboratory facility or a patient service center. Typically, after waiting for his or her turn at that facility or center, a patient is then attended to by a phlebotomist who extracts blood from the patient by way of venipunture. Before venipunture, the phlebotomist selects the correct number and type of vacuum blood collection tubes for the desired number and/or types of tests set forth in the laboratory test request. The phlebotomist ensures that blood from the venipunture fills the correct number and types of tubes. Unless the laboratory tests were ordered STAT or other expedited basis, the patient will wait days or weeks before being notified of the results of the laboratory test. Usually, the notification comes from the doctor or someone in the doctor's office, not from the laboratory that conducted the test.

This process of traditional paper-based test requests and traditional testing infrastructure, has created a legacy system that can be unnecessarily slow and burdened by various limitations.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2014 Theranos, Inc.

SUMMARY

The disadvantages associated with the prior art are overcome by embodiments of systems and methods provided herein.

In one embodiment as described herein, a method is provided comprising displaying a laboratory test menu on a mobile computing device, where the test menu is variable-based on geographic location; selecting one or more tests from said test menu; and using the mobile computing device to send a laboratory test request to a server.

In one embodiment as described herein, a method is provided displaying a laboratory test menu on a mobile computing device, where the test menu is variable-based on geographic location, selecting one or more tests from said test menu; scheduling an appointment for the laboratory test; and using the mobile computing device to send a laboratory test request and appointment information to a server.

In one embodiment as described herein, a method is provided using a mobile computing device to schedule an appointment time for a laboratory test; displaying a laboratory test menu on the mobile computing device, selecting one or more tests from said test menu, wherein the test menu is variable-based on geographic location; and using the mobile computing device to send a laboratory test request and appointment information to a server.

In one embodiment as described herein, a method is provided displaying a laboratory test menu on a mobile computing device, selecting one or more tests from said test menu, wherein the test menu is variable-based on geographic location; displaying pricing of the laboratory tests selected by the user, wherein a total price and line item price are displayed to the user prior to the user sending a laboratory test request; having the user confirm the laboratory test request; and using the mobile computing device to send a laboratory test request and any appointment information to a server.

In one embodiment as described herein, a method is provided displaying a plurality of laboratory test results on a mobile computing device, wherein each of said test results has an acceptable range that is depicted as a shape on a display of the mobile computing device, wherein the shapes of two or more of the test results are normalized such that a longest physical dimension of such shape depicting an acceptable range is displayed in manner that is the same between each of the test results.

In one embodiment as described herein, a method is provided associating insurance coverage information with a user account that is accessible by way of a mobile computing device, wherein insurance coverage of a laboratory test request is confirmed and displayed to the user to show the user's copayment and any other payment requested from the user for a laboratory test request for that user.

In one embodiment as described herein, a method is provided associating a plurality of health care insurances with a user account that is accessible by way of a mobile computing device, wherein insurance priorities in terms of which insurance is charged first is re-orderable by the user and wherein insurance coverage of a laboratory test request is confirmed and displayed to the user to show the user's copayment and any other payment requested from the user for a laboratory test request for that user.

In one embodiment as described herein, a method is provided associating a plurality of dependent patient information with a user account that is accessible by way of a mobile computing device, wherein the associating occurs by way of importing name and other identifying information from a contact list already on or accessible from the mobile computing device.

In one embodiment as described herein, a method is provided associating a plurality of medical provider information with a user account that is accessible by way of a mobile computing device, wherein the associating occurs by way of importing name and other identifying information from a contact list already on or accessible from the mobile computing device.

In one embodiment as described herein, a method is provided creating a user account for accessing laboratory test data from a mobile computing device wherein the user is required to: acknowledge reading and understanding text related to medical, acknowledge reading and understanding text related to terms of use; and reading and acknowledging text related to privacy policy; wherein all of the foregoing is to be completed before the user account is created. Optionally, some embodiments may select one or more data fields as non-mandatory fields so that a user account can be created without necessarily completing those fields or with non-acceptable data entries in those fields.

In one embodiment as described herein, a method is provided capturing an image of a laboratory test request document from a mobile computing device wherein the image is processed after capture to create a corrected image from which data is extracted to include the laboratory test request in association with the user account; wherein the corrected image is created using an image correction algorithm that removes defects in the image associated with fold lines or substantially linear type aberrations in the image; wherein the corrected image is compared to images of known laboratory forms to compare and correct for data captured from the corrected image.

It should be understood that embodiments in this disclosure may be adapted to have one or more of the features described below. In one nonlimiting example, the test menu may be based on where sample will be collected and/or where sample analysis will be conducted. The available tests may be the same in multiple jurisdictions. Optionally, tests from different jurisdictions will have different sets of available tests.

In one embodiment as described herein, non-transitory tangible computer readable media comprising machine-executable code for implementing methods provided herein may be provided as a stand-alone and transportable product (e.g. a DVD, flash drive, magnetic tape, or other form of removable/insertable computer-readable media), such that the program or software stored thereon can be loaded onto one or more different computers, servers, or other computing devices, in order to implement one or more methods provided herein (or elements thereof). In other embodiments, non-transitory tangible computer readable media comprising machine-executable code for implementing methods provided herein may be provided as part of a computing system involving multiple components (e.g. a server or personal computer). In embodiments, a user may interact with software on a server via a client application running on a user device, which is coupled to the server via a network. For example, the software may include a WWW-based interface to allow a remote user/client to access and view account-related information. In embodiments, software running on a server may provide certain features to a user (e.g. a WWW-based interface), while performing various processes/operations on the server.

In one embodiment as described herein, a laboratory test apparatus is provided that is taking the form of a machine readable storage medium (e.g., hard disk, CD, or other medium) (or multiple media) which contains a set of software instructions for execution by a processor for performing methods provided herein.

In embodiments, methods provided herein may be implemented using hardware, software, or a combination thereof. In embodiments, software code may be implemented using one or more processors, which may be distributed between one or more computing devices.

In one embodiment as described herein, a method is provided for allowing a customer to schedule a clinical laboratory test with an application executing on an internet enabled mobile device, where the internet enabled mobile device includes a processor, a memory coupled to the processor and a camera configured to capture a barcode image that has at least a test number encoded therein, the method comprising: causing the processor to display an interface in the application executing on the internet enabled mobile device, the interface for selection of a test option; receiving an input at the processor from the customer indicating, via the application, a selection of the test order to schedule; the application causing the processor to activate the internet enabled mobile device's camera for scanning of a barcode; the application causing automatically or upon a user input, the camera to capture an image, displayed in the application, of the barcode indicating at least a test number corresponding to a test, a patient, or a test and a patient; the application causing the processor to transmit from the application, over a network, to a server, data indicative of at least the test number so that the server can automatically validate the test number by verifying that the test number exists in a database of test numbers corresponding to available tests; receiving information at the internet enabled mobile device, over the network, at least a portion of which is to be displayed in an order review page of the application executing on the internet enabled mobile device; causing the processor to generate a display in the application including the at least the portion of received information in an order review page, wherein the information includes the test number and a test site location where sample for the test will be collected; wherein the information to be displayed in the order review page includes the collection location and an option to change the test site location; transmitting from the internet enabled mobile device, in response to an action by the customer viewing the displayed order review page, to the server and via the network, a confirmation of test appointment.

Optionally, the method of receiving data corresponding to the test information to be displayed in an order review page further comprises receiving a default appointment time and a default date.

Optionally, the method of causing the processor to generate the display comprises displaying an option to facilitate a change by the customer to the default test time and the default test date before transmitting the order confirmation.

Optionally, the method of receiving at the internet enabled mobile device the validation of the test number.

Optionally, the method of causing the processor to generate the display comprises displaying either the most recent sample collection location at which the test order sample was collected or a default location for a patient associated with the test number.

Optionally, the method of causing the processor to generate another display that includes an identified area to assist the customer in positioning the internet enabled mobile device's camera over the barcode.

Optionally, the method of causing the camera to capture the image of the barcode comprises causing the processor to automatically recognize that the barcode is present in the identified area.

Optionally, the method of causing the camera to capture the image of the barcode indicating at least a test number further comprises causing the processor to decode the barcode to determine the test number.

Optionally, the method of causing the processor to transmit, over the network, to the server, data indicative of at least the test number comprises transmitting the captured image, over the network, to the server and further comprises receiving at the internet enabled mobile device at least the test number that was decoded at the server from the captured image.

In a still further embodiment described herein, a non-transitory, computer-readable storage medium is provided wherein the medium has computer-executable instructions stored in a memory, the instructions to be executed on a processor in an internet enabled mobile device for providing an application operable to allow a user access to a test order by scan test form system, the computer executable instructions comprising instructions for: causing the processor to generate a first display in the application executing on the internet enabled mobile device to allow a user to order test(s) from within the application; the application causing the processor to activate a camera in the application executing on the internet enabled mobile device to scan a barcode automatically or in response to a user input; the application causing the camera to capture an image of the barcode indicating at least a test number; the application causing the processor to transmit from the application executing on the internet enabled mobile device at least data indicative of the test number to a point-of-service (POS) server so that the server can verify the test number by verifying that the test number exists in a database of test numbers corresponding to previously filled test medications; receiving over a network at the internet enabled mobile device test information when the test number was verified; the application causing the processor to generate a second display in the application, the second display including the test information on the internet enabled mobile device; wherein the test information to be displayed in the second display of the application includes a test location and an option to change the test location; receiving at the internet enabled mobile device, via the application, a confirmation input from the user; the application causing the processor to transmit from the internet enabled mobile device confirmation information to the server; receiving at the internet enabled mobile device order receipt information from a server; and causing the processor to generate a third display in the application, the third display including the order receipt information on the internet enabled mobile device.

Optionally, the method further comprises instructions for: causing the processor to transmit stored contact information to the server, the stored contact information comprising one of: a stored email address, a phone number associated with the internet enabled mobile device, and a device identification other than a phone number.

Optionally, the method further comprises instructions for: causing the processor to generate on one of the displays an option to facilitate a change by the user to a default test time and a default test date before transmitting the confirmation information.

Optionally, the method comprises causing the camera to capture the image of the barcode comprises causing the processor to automatically recognize that the barcode is present.

In a still further embodiment described herein, a system is provided for receiving a clinical test order for one or more clinical tests, the system comprising: a communication network; one or more internet enabled mobile devices, each internet enabled mobile device having a processor, a memory coupled to the processor and a camera coupled to the processor and the memory; and one or more server computers communicatively coupled to the communication network and the one or more internet enabled mobile devices; one of the one or more internet enabled mobile devices having an application stored thereon; the application configured to cause the processor to display an interface in the application executing on the internet enabled mobile device, the interface for selection of a test ordering option; the application configured to receive an input at the processor from the customer indicating, via the application, a selection of the test order option; the application configured to cause the processor to activate the internet enabled mobile device's camera for scanning of a barcode; the application configured to cause, automatically or upon a user input, the camera to capture an image, displayed in the application, of the barcode indicating at least a test number, the test number corresponding to a test medication and a patient; the application configured to cause the processor to transmit from the application, over the communication network, to at least one of the one or more server computers, data indicative of at least the test number so that the server can automatically validate the test number by verifying that the test number exists in a database of test numbers corresponding to a previously filled test medication; the application configured to receive information at the internet enabled mobile device, over the communication network, at least a portion of which is to be displayed in an order review page of the application executing on the internet enabled mobile device; the application configured to cause the processor to generate a display in the application including the at least the portion of received information in an order review page, wherein the information includes the test number and a sample collection location where the test medication in the test will be filled; the application configured to transmit from the internet enabled mobile device, in response to an action by the customer viewing the displayed order review page, to at least one of the one or more server computers and via the communication network, a confirmation to schedule the test.

Optionally, at least one of the one or more server computers is further configured to transmit to the customer's internet enabled mobile device data corresponding to a default test time and a default test date, wherein the default test time and the default test date are editable by the customer before confirming the order.

Optionally, the application is further configured to allow the customer to edit the default test time and the default test date before confirming the order.

Optionally, at least one of the one or more server computers is further configured to retrieve a default sample collection location for a patient associated with the test number.

Optionally, at least one of the one or more server computers is further configured to receive a store number from the internet enabled mobile device and associate the store number with a particular POS location.

Optionally, at least one of the one or more server computers is further configured to electronically transmit the test order to the determined sample collection location.

A system, comprising: a processor; and a memory communicatively coupled to the processor, the memory having stored therein computer-executable instructions, comprising: a user interface component configured to display patient history and accept user input, wherein the patient history of the user reflects test results for tests performed on the user; a result trending component configured to crawl test data of the user and/or anonymized test data of a plurality of other users, wherein trending data histories reflect test results by respective other users of the plurality of other users, and identify based on the test results of other users, the results the users should try to achieve based on those other users which are selected based on criteria of interest.

A non-transitory computer-readable medium comprising computer-readable instructions that, in response to execution, cause a system including a processor to perform operations, comprising:

Using a mobile application to self-order a laboratory test without a physician's order, wherein such self-ordering is only activated based on geographic location of a selected test site that allows for such self-ordering.

The non-transitory computer-readable medium wherein the operations further comprising: self-ordering a plurality of laboratory tests.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DESCRIPTION OF THE SPECIFIC EMBODIMENTS

Figure 1:
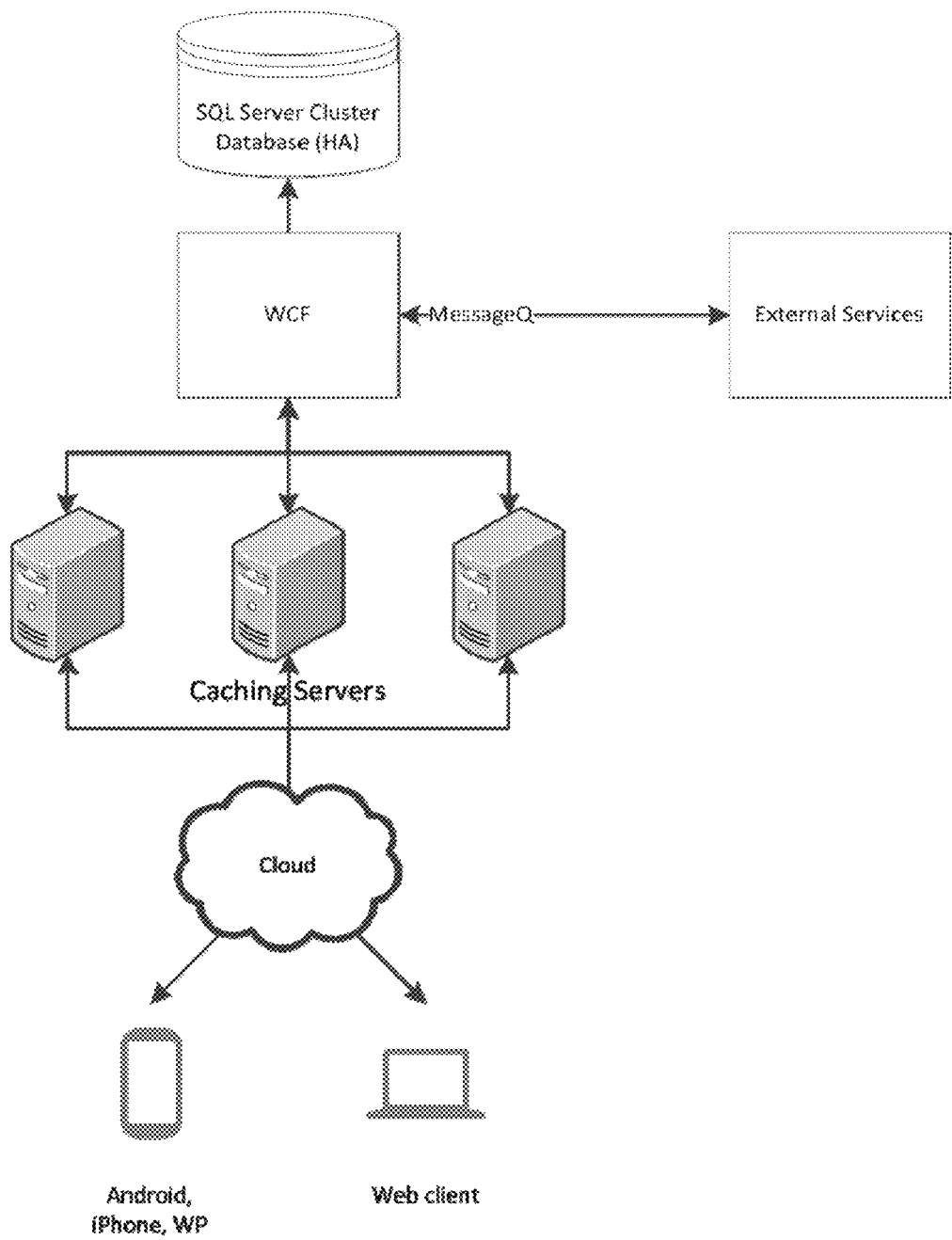
FIG. 1 shows a system according to at least one embodiment described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

It should also be understood that for any and all of the user interface figures shown herein, a colored icon such as but not limited to a green circle or other shape may be used to indicate where a user may tap, click, or otherwise select an object, item, or other feature visible on a user interface.

Figure 2:
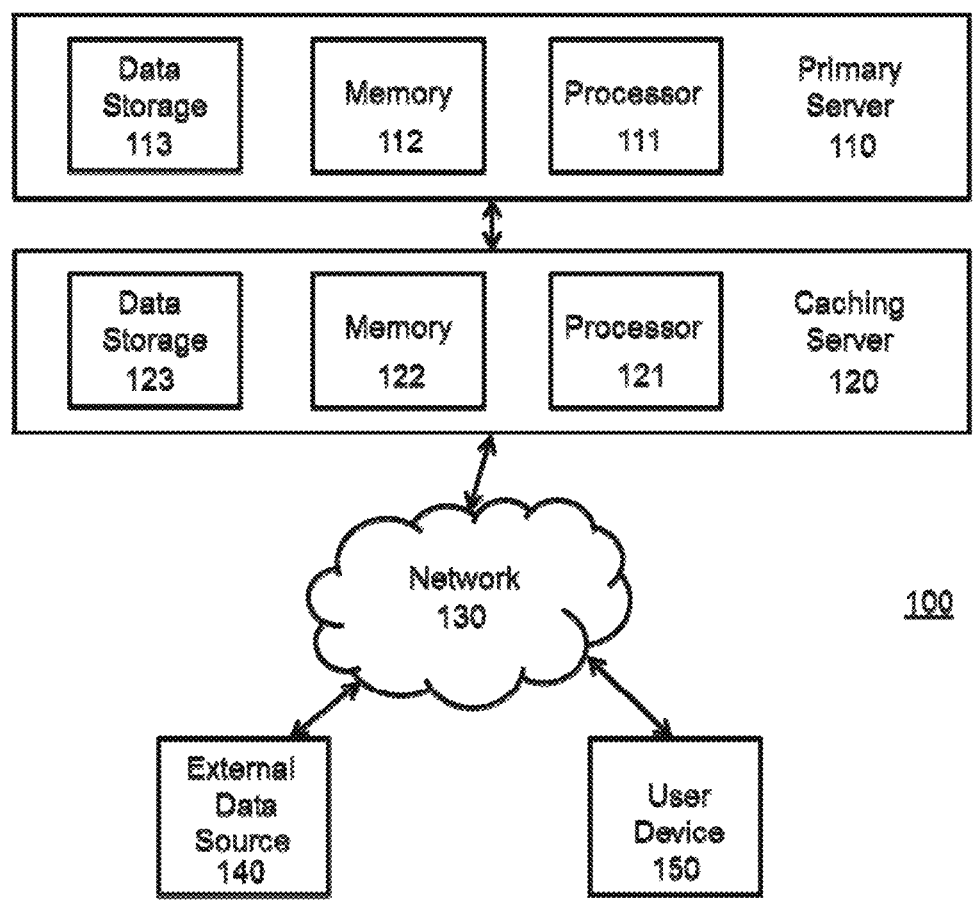
FIG. 2 shows another system according to at least one embodiment described herein.

Referring now to FIGS. 1 and 2, exemplary embodiments of a system for use with the user interfaces, workflows, and/or other features is described herein. As seen in FIG. 1, there may be one or more caching servers that are in place to respond to data requests. In some embodiments, the caching server may not have the information requested. In such a scenario, the requesting device can already know to direct the request to the server with the data base, or optionally, for the caching server or other intermediary to direct the request to the server with the data. By way of example, the caching server can provide information that may be relevant to a geographic region or other factor for the server to be located in manner that responds the data request. Some embodiments may have scheduling information, location information, services information, or the like for users and/or locations in certain areas.

In one embodiment as seen in FIG. 2, the system 100 may comprise, for example, a primary server 110, a caching server 120, a network 130, an external data source 140, and a user device 150. The primary server 110 may store or process data, such as laboratory test-related information. The caching server 120 may also store or process data, although its major purpose may be to temporarily store copies of content which is also available in the primary server. The network 130 may be any structure which can support the operable connection of and data transfer between two or more computing devices, such as a local area network (LAN) or a wide area network (WAN), and may include, for example, an intranet or the Internet. The external data source 140 may be any computing device which may store, transmit, receive, or gather data that may be accessed by or sent to a server of the system. The user device 150 may be any computing device with which a user may review, input, or change laboratory test-related information. As used herein, a "computing device" refers to any device which may store, transmit, receive, gather, or process digital data, and may include, for example, servers, personal computers, data storage units, hard drives, portable digital media, smartphones, computer systems, mobile devices, external data sources, user devices, and websites. In embodiments, systems or elements thereof described herein may be implemented as a cloud-computing system.

A primary server 110 may contain, for example, at least a processor 111, a memory unit 112, and a data storage unit 113. In this non-limiting example, the processor 111 of a server may be a hardware structure which performs computational operations of a computer program. In embodiments, a processor 111 may carry out instructions stored in a tangible computer readable medium. The processor 111 may contain one or more microprocessors. A memory unit 112 is a structure for storage of digital information which typically uses volatile storage and is rapidly or directly accessible by a processor (e.g. random access memory (RAM)). A data storage unit 113 is a structure for storage of digital information which typically uses non-volatile storage, and which typically has a much larger storage capacity than a memory unit 112, but is less quickly accessible by the processor 111 than the memory unit (e.g. hard drive). In embodiments, the memory unit 112 or data storage unit 113 may store non-transitory computer readable media, which may include, for example, code, logic, or instructions for performing methods provided herein. A primary server 110 may have any number of processors 111, memory units 112, or data storage units 113 (e.g. 1, 2, 3, 4, 5, 6, 7, 8, 9, 10, 15, 20, 25, 50, 100, 1000, or more of any or each of the processors, memory units, or data storage units). A primary server 110 may also contain other components, such as a removable media drive (which may accept, for example, CDs, DVDs, floppy disks, or magnetic tape-based storage), input-output (I/O) channels, buses, network interfaces (wired or wireless structures for facilitating data transfer between a server a network), or power supplies. A primary server 110 may have a variety of different shapes and structures. For example, a primary server 110 may be a dedicated server, or it may be part of a computer which contains other features (e.g. a monitor, peripherals, etc.). In some embodiments, the primary server 110 may be part of, for example, a personal computer or a smart phone.

Optionally, a system provided herein may contain non-transitory tangible computer readable media. Computer readable media can be any available media which can be directly or indirectly accessed by a processor or server of a system provided herein. Computer readable media may include volatile and nonvolatile media, as well as removable and non-removable media. Computer readable media may be implemented in any method or technology for storage of information, such as computer readable instructions, data structures, program modules, or other data. Computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage device, or any other medium which can be used to store information and which may be accessed by a processor or server.

Optionally, a server may be operably connected to one or more external data source 140 (e.g. a website with information of interest, a GPS associated with a computing device of interest, a different server, a hard drive); the server may obtain information from such sources as-needed or at regular intervals. In embodiments, a server may include data mining hardware or software, such as software configured to search the Internet or predetermined web sites (e.g., "weather.com") on the internet to obtain data of interest. In embodiments, an external data source 140 may be a data storage unit operably connected to the server. A server may have load balancing, task management, and backup capacities. The components of a server may be within a single housing unit, or they may be distributed between two or more housing units. A server may be implemented as a distributed network of processors, memory, and storage units. A server may contain or be operably connected to a database (for example, the database may be in a data storage unit of the server or in an external data source). The processor of a server may run a computer program or software, the instructions of which may be provided from, for example, a data storage unit, removable media, or a data storage unit operably connected to the server. In embodiments, two or more servers may act together to function as a server. Servers may communicate with any number and type of computing devices. The server may engage in one-way or two-way communication with computing devices. Other server components or configurations not explicitly discussed herein but known in the art may be included in servers and systems described herein.

By way of non-limiting example, the primary server 110 may contain or be operably connected one or more databases of information relevant to laboratory testing. For example, databases may contain information relating to users or patient accounts, such as patient home addresses, patient contact information (e.g. phone number, e-mail address), billing information, emergency contact information, insurance information, appointment histories, medical records, user login names and passwords, patient healthcare provider information, or other information. The primary server 110 may, with the aid of a processor, use data from one or more sources to perform methods relating to laboratory test analysis or scheduling Optionally, the caching server 120 may have any of the components or configurations of the primary server 110 described elsewhere herein. Generally, the caching server 120 is optimized for temporary storage of frequently-accessed content from the primary server 110, in order to increase the speed at which the content can be delivered to a client/user and to decrease the number of operations to be performed by the primary server 110 (and in turn, to increase the performance of the primary server 110). The caching server 120 may store content in either or both of the memory unit 122 or data storage unit 123. In systems and methods provided herein, the caching server may store, for example, appointment information for one or more health service centers. The caching server 120 may be configured to regularly update from the primary server 110 its cached content. In embodiments, a caching server 120 may be located in a particular geographic area, and may be configured to respond to data requests from users the same or related geographic areas. For example, a first caching server 120 could be provided in North Carolina to respond to requests based in the eastern United States, a second caching server 120 could be provided in Texas to respond to requests based in the central United States, and a third caching server 120 could be provided in California to respond to requests based in the central United States. In embodiments, two or more caching servers 120 may be operably connected to a single primary server 110. In other embodiments, two or more caching servers 120 may be operably connected to two or more primary servers 110. In embodiments, a system provided herein may contain more caching servers 120 than primary servers 110, more primary servers 110 than caching servers 120, or equal numbers of primary servers 110 and caching servers 120.

Optionally, the network 130 may be any structure which can support the operable connection of and data transfer between two or more computing devices, such as a local area network (LAN) or a wide area network (WAN), and may include, for example, an intranet, an enterprise private network, the Internet, cellular, or satellite networks. The network may include, for example, one or more of wireless connections, wired connections, or fiber optic connections. Computing devices (e.g. servers, external data sources, and user devices) may connect to the network 130 by wired or wireless technologies. For example, a computing device may connect to the network 130 via wired technologies such as a dial-up connection with a modem, a direct link such as TI, ISDN, cable, Firewire, USB, or Ethernet wire. In other examples, a computing device may connect to the network 130 via wireless technologies such as Bluetooth,®, infrared (IR), radio frequency (RF), ZigBee, Z-wave, wireless USB, code division multiple access (CDMA) or global system for mobile communications (GSM). In embodiments, data may be encrypted before it is transmitted over the network 130.

Optionally, the external data source 140 may be any computing device which may store, transmit, receive, or gather data that may be accessed by or sent to a server of the system. External data sources include, for example, other servers, hard drives (e.g. IDE, ATA, or SATA drives), databases, personal computers, data storage units, hard drives, portable digital media, smartphones (e.g. Apple iPhone, Android-enabled phone), mobile devices, and computer systems, global positioning system (GPS) devices. An external data source may be portable or non-portable/at a fixed location. In embodiments, an external data source 140 may be capable of obtaining geolocation data, such as by wireless triangulation or a GPS system. In embodiments, an external data source 140 may be on or associated with a subject (e.g. on a subject's wrist or in a subject's pocket or handbag). The external data source 140 may be a portable computing device in proximity to the subject such that the measured location of the device corresponds to the location of the subject. The device may be a portable computing device the subject carries for other purposes. For example, the device may be a smart phone, such as an iPhone or Android-enabled phone, capable of gathering geolocation data, such as with the aid of a GPS module of the device. The device may be an iPad or other portable computing device, such as a watch capable of gathering geolocation data. A client-server relationship, peer-to-peer, or a distributed relationship, may be provided between the external data source 140 and a server of the system. In embodiments, an external data source 140 may communicate directly or indirectly with a server. For example, an external data source 140 may have a direct wired linkage to a server. In another example, an external data source may communicate wirelessly with a server. In another example, an external data source 140 may communicate with a server when the external data source is connected to a personal computer via a wire, and when the personal computer is connected to the Internet. In embodiments, the external data source 140 is operatively coupled to the primary server 110. The external data source 140 may be coupled to the primary server 110 such that data travelling between the external data source 140 and the primary server 110 passes through the caching server 120 as it travels between the external data source 140 and the primary server 110. Alternatively, the external data source 140 may be coupled to the primary server 110 such that data travelling between the external data source 140 and the primary server 110 does not pass through the caching server 120 as it travels between the external data source 140 and the primary server 110. In embodiments, the system may be configured such that the external data source 140 is operatively coupled to the primary server 110 without passing through or involving the caching server 120. With systems and methods provided herein, 1, 2, 3, 4, 5, 10, 15, 20, 25, 100, 1000 or more external data sources 140 may be in communication with a server.

Optionally, the user device 150 may be any computing device with which a user may review, input, request, or change laboratory-test related information. User devices may include, for example, personal computers, tablet computers, smartphones (e.g. Apple iPhone, Android-enabled phone), mobile devices, or computer systems. A user device may be portable or non-portable/at a fixed location. A user device 150 may contain one or more user interfaces. User interfaces may provide information to a user, obtain inputs from a user, or both. A user interface may have a display, such as a cathode ray tube, plasma, liquid crystal display (LCD), or light-emitting diode (LED)—based display. In embodiments, a user interface may include a graphical user interface (GUI) configured to display information to a user on a display, such as appointment time and availability information. A GUI may also be configured to receive information from a user, such as by capacitive or resistive touch-screen functions. In some situations, user interfaces may include camera for video or still images, a microphone for capturing audible information (e.g., a subject's voice), speakers for providing audible information, a printer for printing information, or a projector for displaying images and/or video on a predetermined viewing surface. Other user interfaces of a user device 150 may include, for example, a keyboard, touch pad, or a computer mouse. A user device may contain a processor and local memory and data storage.

In at least some embodiments, certain computing devices may function as both an external data source 140 and a user device 150 for systems provided herein. For example, a GPS receiver-containing tablet computer may both: i) obtain patient location data which is provided to a server running a software program described herein (and thus, function as an external data source 140), and ii) provide a user interface such as a touch screen which may display and receive user input regarding appointment times (and thus, function as a user device 150). In other embodiments, certain computing devices function as either an external data source 140 or a user device 150. For example, a stand-alone hard drive operatively coupled to a primary server 110 is an external data source 140 but not a user device 150. In another example, a computer having a display at a health service center to display appointment time information for patients may function as a user device 150 but not an external data source 140.

In at least some embodiments, a user may be able to interact with software on a server through a client application running on a user device 150. A client application may be, for example, a World Wide Web (WWW)-based interface. A WWW-based interface may be provided, for example, at a specific URL (e.g. a web page), which users may access via the network 130 through a user device 150. A user may request a WWW-based interface at a specific URL, and the content may be delivered to the user device from the primary server 110 or caching server 120. In embodiments, users may input information on a WWW-based interface, and the information may be provided to one or both of the primary server 110 or caching server 120. In embodiments, a WWW-based interface may permit a user to log in to a user account, to permit the user to access one or more interconnected web pages (e.g. web pages associated with the user account). In embodiments, a WWW-based interface may provide laboratory test—related information. With the WWW-based interface, a user may optionally be able to, for example, view appointment-related information, request an appointment, change an appointment date/time, cancel an appointment, or provide special instructions or comments relating to a past or upcoming appointment.

In addition to the system components and configurations described above and elsewhere herein, it is also noted that other suitable system components and configurations may be used with systems and methods provided herein. For example, embodiments of methods provided herein can be implemented in a computing system that includes a back-end component (e.g. a primary server) and a front-end component (e.g. a user computer having a GUI or Web browser through which a user can interact with a computer software for performing methods provided herein), in which the back-end component and front-end component are interconnected by any combination of hardware and software for digital data communication. In other examples, embodiments of methods provided herein can be implemented using a single computing device (e.g. where the computing device stores relevant data, contains one or more processors for performing operations described herein, receives user information, and displays information to a user). Also, it is noted that the relationship between objects depicted in FIG. 2 and elsewhere here is exemplary, and other relationships are within the scope of systems and methods provided herein. For example, although FIG. 2 depicts an external data source 140 being connected to a primary server 110 via a network 130, in embodiments, an external data source may 140 may directly link to a primary server 110 (i.e. without connecting through a network 130).

Architecture

In one non-limiting example, a high-level architecture for the system herein may include both hardware and software applications, as well as various data communications channels for communicating data between the various hardware and software components. In this non-limiting example, the system 100 may be roughly divided into front-end components and back-end components. The front-end components are primarily disposed within a point-of service network such as but not limited to one or more stores, retail sites, shopping malls, kiosks, medical offices, non-hospital medical offices, and/or pharmacies. For pharmacies, the front-end components comprise a number of pharmacy workstations. The workstations may be local computers located in the various pharmacies throughout the retail network and executing various pharmacy management-related applications. For any of the embodiments herein, web-enabled devices (e.g., personal computers, cellular phones, smart phones, web-enabled televisions, etc.) may be communicatively connected to point-of-service location(s) and the system through a digital network, as described herein.

It should be understood that the front-end components could also comprise a plurality of facility servers disposed at the plurality of pharmacies instead of, or in addition to, a plurality of pharmacy workstations. Each of the pharmacies may include one or more facility servers that may facilitate communications between the web-enabled devices and the back-end components via a digital network, described below, and between the terminals, of the pharmacies via the digital network, and may store information for a plurality of customers/employees/accounts/etc. associated with each facility. Of course, a local digital network may also operatively connect each of the workstations to the facility server. Unless otherwise indicated, any discussion of the workstations also refers to the facility servers, and vice versa. Moreover, environments other than the pharmacies, such as the kiosks, call centers, and Internet interface terminals may employ the workstations, the web-enabled devices, and the servers. As used herein, the term "retailer" refers to any of these points of contact (e.g., call centers, kiosks, Internet interface terminals, etc.) in addition to the retail store locations, etc. described above. As used herein, the term "point-of-service provider" refers to any of these points of contact (e.g., call centers, kiosks, Internet interface terminals, etc.) in addition to the point-of-service physical locations, etc. described above.

In one non-limiting example, the front-end components may communicate with the back-end components via the digital network. One or more of the front-end components may be excluded from communication with the back-end components by configuration or by limiting access due to security concerns. For example, the internet enabled devices may be excluded from direct access to the back-end components.

In one non-limiting example, the digital network may be a proprietary network, a secure public Internet, a virtual private network or some other type of network, such as dedicated access lines, plain ordinary telephone lines, satellite links, combinations of these, etc. Where the digital network comprises the Internet, data communication may take place over the digital network via an Internet communication protocol.

It should be understood that different numbers of processing systems, collection locations, and devices may be utilized. For example, the digital network (or other digital networks, not shown) may interconnect the system to a plurality of included central processing systems, hundreds of point-of-care locations, and thousands of web-enabled devices. According to the disclosed example, this configuration may provide several advantages, such as, for example, enabling near real-time uploads and downloads of information as well as periodic uploads and downloads of information. This provides for a primary backup of all the information generated in the express test order process. Alternatively, some of the point-of-care locations such as but not limited to pharmacies may store data locally on the facility server and/or the workstations.

Although data that is transmitted may be encrypted, to further protect patient privacy when such information is displayed, printed, or otherwise conveyed, some or all of certain fields may be masked. For example, the drug name and strength or other information may be masked but for a numerical portion of medication strength (i.e., "500") or a patient name (e.g., "Max Jones") may be masked but for one or two characters (e.g., Mxx Jxxxx).

Embodiments of the systems and methods described above are contemplated in which the system 100 may be implemented in a minimalistic interface suited for a web-enabled mobile phone, smart phone, personal digital assistant, etc., or in an application for execution on such a device. For example, an application for a mobile device (e.g., the web-enabled devices) may be developed for a mobile platform such as the Android, webOS, or iOS mobile technology platforms, originally developed by Google Inc., Palm Inc., and Apple Inc., respectively. Accordingly, the application may interact with the server described above. Additionally or alternatively, the application may interact with a server specially implemented and/or designated to provide the express test order service in cooperation with the application. Moreover, an application designed specifically to interact with the system may provide the field for entering an email address or, alternatively, may transmit to the web server (or other server) a stored email address that the user has associated with the mobile device. As another option, the application could transmit a phone number associated with the device, an application ID specific to the application instance operating on the mobile device, or other data (e.g., an internet protocol ("IP") address or a media access control ("MAC") address) associated specifically with the mobile device. Accordingly, the system may send one or more notification messages when the test time is approaching or if the user is physically near the test location. The notification may be transmitted to the email address entered by the user, to the email address transmitted automatically from the mobile device, to the mobile device as a text message, to the application as a notification or message displayed within the application, etc.

Mobile-specific web sites may use pared-down versions of HTML web pages, or may implement other "lightweight" web pages written in languages including Extensible Hypertext Markup Language (XHTML) or Wireless Markup Language (WML).

Some embodiments may allow the user to complete an order with as little as three inputs into two web pages. That is, if the customer navigates directly to a page having a test number field the customer may (1) enter a test number, (2) click the continue button, and (3) click the submit button after reviewing the test order.

In embodiments implementing a mobile device application, the mobile device includes a processor and a memory. The application may be implemented as a series of machine-readable instructions for performing the various tasks associated with receiving information at, displaying information on, and transmitting information from the internet-enabled device. Of course, the application itself may, at various times, be stored on the internet-enabled device, a server (not shown) from which users download the application to a mobile device, a compact disc, a DVD, etc.

The image capture device may be used by the application to capture an image of a barcode. Throughout this application the use of the word "barcode" is intended to be generic and inclusive of all types of barcodes. Barcodes could be, for example, the conventional rectangular segment barcodes as well as two dimensional QR codes or matrix barcodes. Most QR codes have black modules arranged in a square pattern on a white background. Smaller versions may be referred to as micro QR codes and design QR codes include a picture or logo to enhance conversion rates. In some embodiments, the mobile device application may interpret the captured barcode image to generate test data (such as a test number) and transmit the test data to the server. In other embodiments, the mobile device application may transmit the barcode image to the server, which may interpret the barcode image to obtain test data. In still other embodiments, the mobile device application may transmit the barcode image to a third-party server (not shown) which may interpret the barcode image to obtain test data and transmit the obtained test data to the server.

A user executes the application on the mobile device to display a home screen of the application. The user selects to a test to order and the application displays a test scanning screen and activates an image capture device (i.e., a camera). The user scans a barcode to determine the test order number by aligning the camera with a barcode on a receipt, test order, or other documentation, so that the barcode appears in an area of the screen. The mobile device application, in some embodiments, may automatically recognize that a barcode is present in the view of the image capture device, and may act automatically to capture and/or interpret the barcode. In other embodiments, the mobile device may require the user to cause the image capture device to capture an image, before the mobile application interprets or otherwise uses the barcode image. In still other embodiments, the mobile device application may transmit the captured barcode image to a third-party server (not shown) and the third party server may interpret the barcode image and transmit a test number to the server or back to the mobile device application for transmission to the server.

In some embodiments, the control that allows the user to change the selected store may activate—or give the user an option to activate—a geolocation device (e.g., a global positioning system (GPS) device) in a web-enabled device, particularly if the device is a mobile device. The geolocation device may, by itself or cooperating with another application or an online service, provide the mobile device application with an indication of the mobile web-enabled device's current position, which the mobile device application may use to determine the closest store at which the requested tests can be filled.

As described the mobile device application displays the default time, date, and location of test. If the user selects to edit the time, the mobile device application displays a pick list of times and then receives the time selection input from the user before returning the display to the time, date, and location of test (though no longer the default time). Similarly, if the user selects to edit the date, the mobile device application may display a pick list of dates and then receives the date selection input from the user before returning the display to the time, date, and location of test. Lastly, if the user selects to edit the test store, the mobile device application may transmit a request to a store finder service/routine which may run on a server. The mobile device application may receive a response from the service/routine. After receiving a test location selection input from the user, the mobile device application may return the user to the time, date, and location screen.

It should be recognized that different mobile devices may implement different mechanisms for user input. In the examples described above, the mobile phone is assumed to have a touch sensitive display screen. Accordingly, "buttons" which are displayed on the screen and are not physical buttons, are "pressed" by touching the screen in the area of the button. However, those of ordinary skill in the art will readily appreciate that such user interface controls may be accomplished in other manners, such as using soft-keys, navigating controls using navigation buttons on a keyboard or using a roller ball, selecting numbers corresponding to different controls, entering information on a keyboard, etc. Optionally, future embodiment may have interfaces on multiple "screens" such as but not limited to one or more screens on a lateral, back, or other side portion of the device. Some may have curved screens that have portions not in the same plane as a primary portion of the screen.

User Interface

Figure 3A:
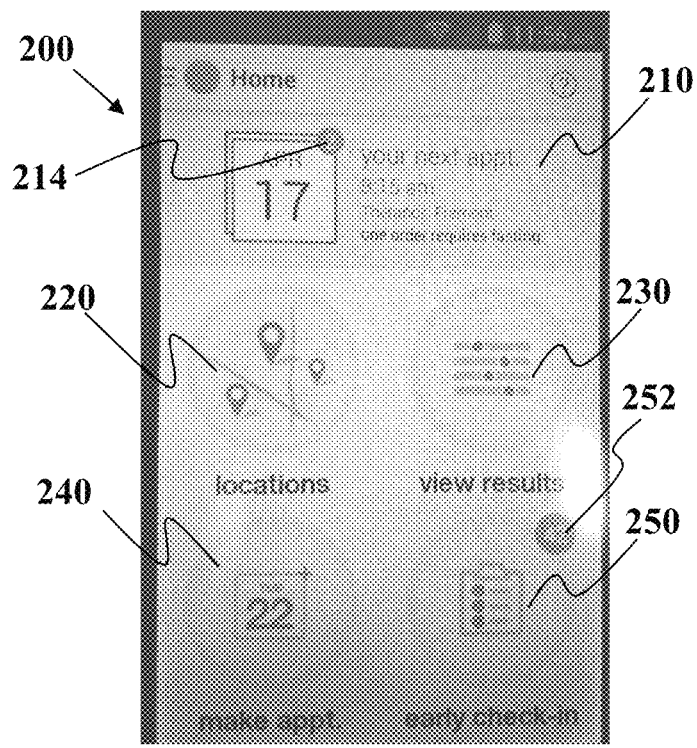
FIGS. 3A and 3B show various embodiments of user interfaces and/or workflows as described herein.
Figure 3B:
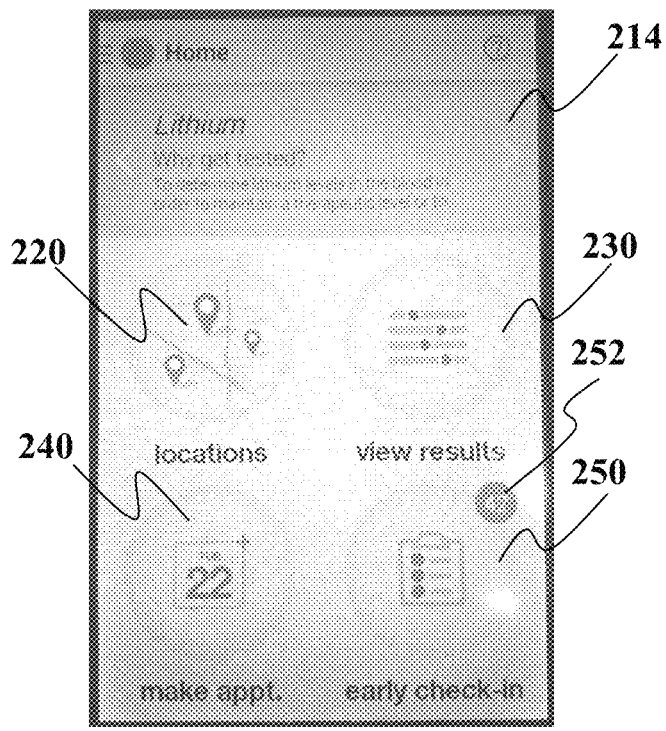

Referring now to FIGS. 3A to 3B, various screenshots are shown of user interfaces of various embodiments of an application that may be run on a client computing unit, such as but not limited to, an internet-enabled mobile computing device. In one non-limiting example, the unit may be a tablet computer. Optionally, it may be a handheld computer. Optionally, it may be a cellular telephone. Optionally, it may be a smartphone. Other examples of mobile and/or portable computing devices including wearable computing devices are not excluded.

Referring now to FIG. 3A, one embodiment of a homepage 200 associated with the application is shown. As seen in FIG. 3A, this homepage 200 may include at least one or more of the following. Optionally, some embodiments may have two or more the following. For example, FIG. 3A show a banner region 210 wherein information useful to the user can be displayed. In one embodiment, the information in banner region 210 will auto scroll, auto update, or self-update to provide different types of information to the user in a sequential or random order. One embodiment may show the information for a user's next appointment. It may show one or more of the following: a graphical representation of a calendar date of the next appointment, location where the user should go for next appointment, the exact time of the next appointment, a numeral 212 indicating how many lab tests may be conducted, and/or a display of any special requirements for the lab test (such as but not limited to one order requires fasting, orders requiring consumption of specific items during or prior to testing, etc. . . . ). If a user has more than one appointment, that number may also be displayed alone or along with select information associated with the appointment.

FIG. 3B shows another display 214 in the banner region provides medical information about lab tests. In one embodiment, the medical information to be display is selected to be displayed to the user based on one or more of lab tests that the user has upcoming, the user has completed, or that they system, based on the user information, thinks the user may want to know. In one non-limiting example, it shows medical and other information about relevant laboratory tests, prioritizing ones in the user's lab order.

Referring again to FIG. 3A, this non-limiting example of a home screen shows that it may include an icon 220 for selecting the finding of nearby or user selected locations of wellness centers or other facilities where a user can go for sample collection. One embodiment may optionally include an icon 230 for selecting viewing test results. This may include not only the current results but also test result history. One embodiment may optionally include an icon 240 for selecting scheduling an appointment at a nearby or a user selected location for sample collection. One embodiment may optionally include an icon 250 for early check-in for notifying a wellness center or other sample collection location that a user is on his or her way to that location. As seen in FIG. 3A, some embodiments may include a numeral 252 indicating the number of appointments where the user has checked-in early.

Optionally, the home screen page may be different for first time user, a returning user with new lab results and a new lab order, and/or a returning user with a scheduled appointment. Optionally, the home screen page that is a dashboard screen that will display summary of actual results instead of links or icons that take a user another screen where results are shown. On the returning user page, some embodiments may also include links to past laboratory or other test results and/or to pending laboratory orders. Optionally, in at least some embodiments, there may be a screen showing a health tracker, dashboard, or status page associated with one or more user, medical professional, drug company, and/or other party selected factors to display regarding a patient's health and/or other specific condition. Optionally, the page showing the health tracker and/or status page may have color codes associated with certain factors, such as but not limited to caution or other alert level. Optionally, some may display colors, icons, or visuals associated with a good result. Some embodiments may also include numeric values or other more detail information displayed in, next to, near, or otherwise associated with the color coded area. Optionally, a health tracker, dashboard, or status page may also include information about any upcoming appointments and/or laboratory orders.

FIGS. 3A to 3B shows that by tapping on an icon or other symbol, a user can also reveal or invoke a menu showing navigation to different information displays. The tapping may occur through the use of a user's finger, a stylus, a pointer, or other selection device. Optionally, some embodiments may use an image capture device such as but not limited to a camera as part of a tracking system to determine if the eyes, eyelids, or other portion of the user, indicates a selection. As seen in FIG. 3, some embodiments show a variety of actions or options available for the user. By way of example and not limitation, the menu may slide out from one side of the screen, from the top down, from the bottom up, and/or may fade-in. In one non-limiting example, the tabs shown in the menu can be as shown or can include additional categories not shown. Optionally, it can also show fewer tabs. As seen in FIG. 3, some embodiments may still show a portion of the underlying page (in this example, showing the health tracker page) either shifted to one side of the menu, or optionally, covered by the menu.

Figure 4A:
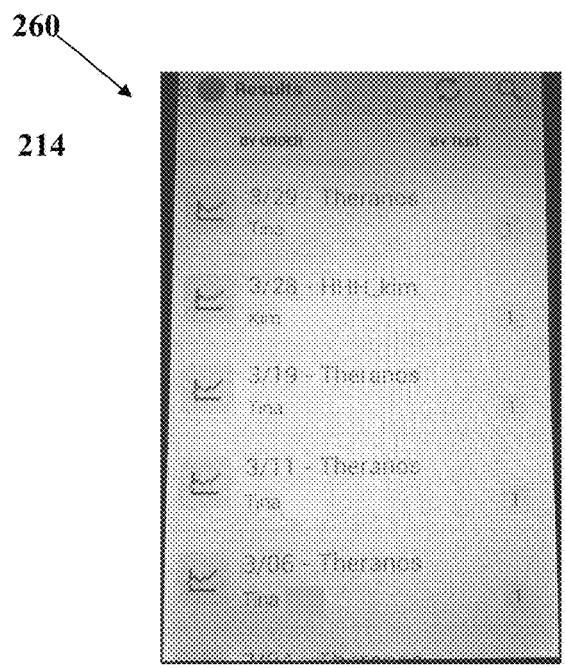
FIGS. 4A to 4H show various embodiments of test result user interfaces and/or workflows as described herein.

Referring now to FIGS. 4A to 4H, various screenshots are shown when navigating the application workflow through the test result icon 230. Referring now to FIG. 4A, a screen page 260 is shown listing test results by order, which in this non-limiting example is the date of the test result.

Figure 4B:
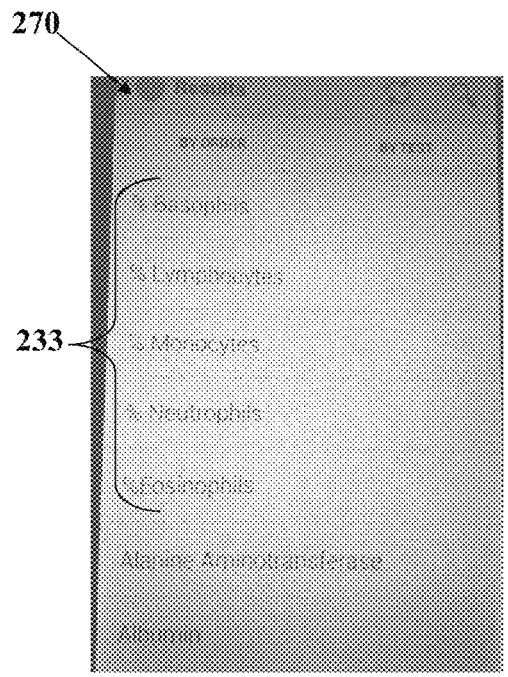

Optionally, as seen in FIG. 4B, the results may be sorted in one or more other manners such as but not limited to test type as shown in screen page 270. FIG. 4B shows that the "by test" listing can sub-group certain tests that are related such as but not limited to leukocyte information 233 related to types of white blood cells in the blood test.

Referring back to FIG. 4A, it can be seen in this non-limiting example that the information to be displayed may include but is not limited to the date of the test, the user name, the actual name, the number of appointments, the number of lab tests, and/or other information associated with the test result. As seen in FIG. 4A, the test results may be for one user, or if on a family account, may include results for one or more other subjects that may be part of the family or other grouping where that individual, if of age, has consented to share their test result information. In one embodiment, a parent or legal guardian can access results of their dependent minors without direct consent from the minor.

Figure 4C:
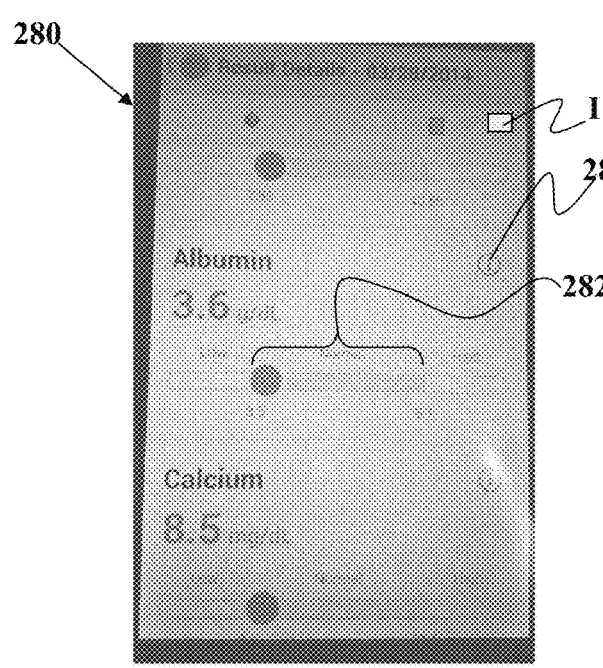

FIG. 4C shows one non-limiting example of a screen page 280 showing test result in a numeric and/or a graphical manner. Optionally, some embodiments only present the information in graphical manner. Optionally, some embodiments may present the information as a combination of text and numerals. As seen in FIG. 4C, it should be understood that the test results can be displayed on any of various devices a user may use to access their test results. By way of non-limiting example, test results can be shown on a personal computer, a mobile phone, and/or a tablet computer.

Some embodiments can change the color of the dots, data markers, test value, or the like on the data displayed to indicate if the reading is one of concern. For one non-limiting example, some may use the usual red, yellow, and green for test result colors. Optionally, some may use other colors in that spectrum leading from green to red, wherein red is an undesirable test result. Some embodiments can change the color of letters or in the present embodiment, the color of the dot in the logo so that it can go from green, to yellow, and/or to red if the results of the tests are on-balance in an undesirable range.

FIG. 4C also shows that in some embodiments, the "normal" result data range 282 is normalized so that all of the result bars from the various lab tests are of substantially the same length. In this manners, this presents data in a manner that the user may be able to scan visually to see if any results are outside the normal range. FIG. 4C also shows that there may be an information icon 284 associated with each result so that a user has the option to receive more information about what was tested.

It should also be understood that, in some embodiments, the data range may be shifted so that the out-of-range results are highlighted such as but not limited to a) showing primarily the high results if that is where the out-of-range results are, b) showing primarily the low results if that is where the out-of-range results are, and/or c) the entire range if there are both high and low out-of-range results. For out-of-range results, in addition to or in place of changing the color of the dot, number value, or other data marker, some embodiments may change the entire color of the bar, the height of the bar, the width of the bar, highlight the background of the bar, and/or other visual indicator.

Referring still to FIG. 4C, it should be understood that some embodiments may have more detailed scale bars or lines such that there are descriptors of deficient, insufficient, high, toxic, or the like for various out-of-range test results. In this manner, a user can, in addition to color or other indicator, have a text descriptor of how the results compare. It should also be understood that some embodiments can have a balloon-pop-up or marker for the test result. By way of non-limiting example, this pop-up can include the numeric value for the test result and/or include the coefficient of variation or other additional information about the test result numeric value.

Figure 4D:
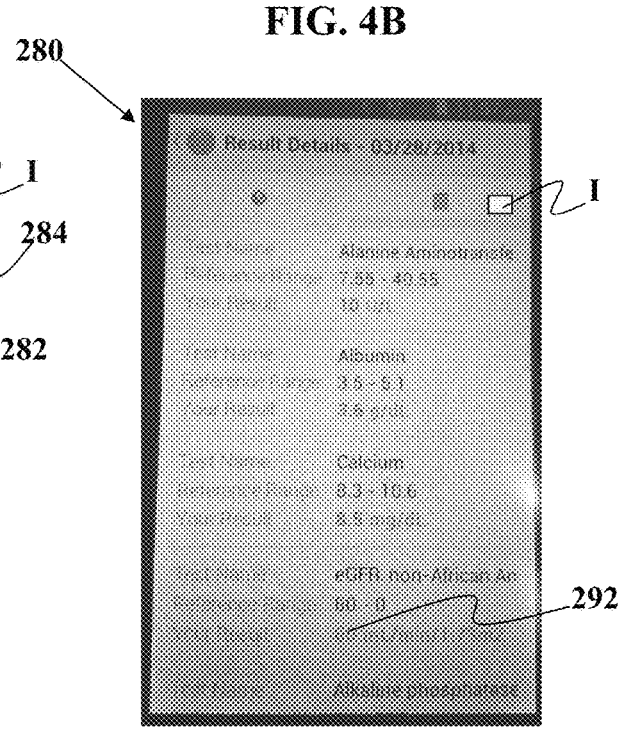

Referring now to FIG. 4D, test results may also be reported in text, numerals, or combinations thereof as seen in screen page 290. As seen in FIG. 4D, out-of-normal-range result(s) 292 may be highlighted in a visual manner such as but not limited a font color different from font color for normal results, a font size (larger or smaller) than font size font size for normal results, a different front from the font for normal results, and/or other indicators to a user that the result is not in the normal range.

In some embodiments, the results may have an overall color or other indicator (visual shape, color, size, position of data marker, or the like) of test results being in range. If a certain number of test results are out of range, then an overall indicator I can show a different color, text, or other indicator to let the user know that the overall results were of a concern. By way of non-limiting example, the number or other factor that results in this change in indicator I can be set by a medical professional, by the user, by a laboratory, and/or by another authorized entity. Optionally, some smaller sized user interfaces, such as mobile phones or the like, can scale or otherwise adjust the display so that the results are still shown, but an indicator I may be removed or otherwise shown in reduced size or at other locations on the screen if space is insufficient. Some optional methods for indicator I can be a change in color or text I in the title bar, background, or other screen area.

Figure 4E:
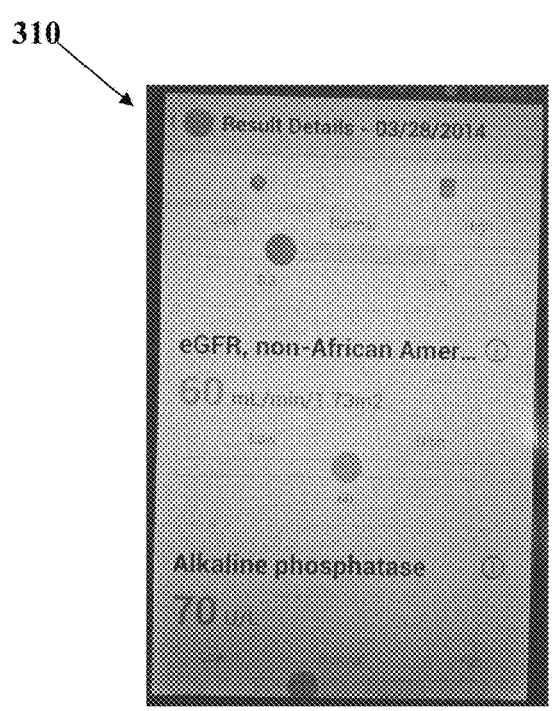

Referring now to FIG. 4E, one non-limiting example of a non-normal range result is displayed on screen page 310. As seen in FIG. 4E, the numeric value of the result may be visually distinguished by a different color than normal results. This embodiment may also be configured so that the data marker can also be a visual indicator such as but not limited to being a different color, different size, different shape, and/or other indicator showing a difference from normal range results.

Figure 4F:
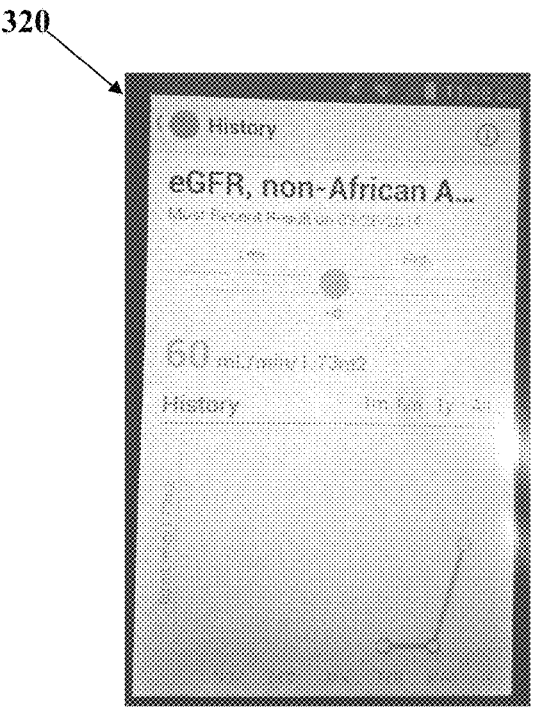

Referring now to FIG. 4F, selecting a specific assay result from the test "results details" screen page will lead us to screen page 320 which shows a history of test results for that specific assay. By way of non-limiting example, FIG. 4F shows one region with the numeric value of the test result, a display of the data range, and a graph showing the history of results of the assay from current and previous testing event(s). This historical view of the results may be represented as a line graph, bar chart, or other visual representation to convey information to the user.

Figure 4G:
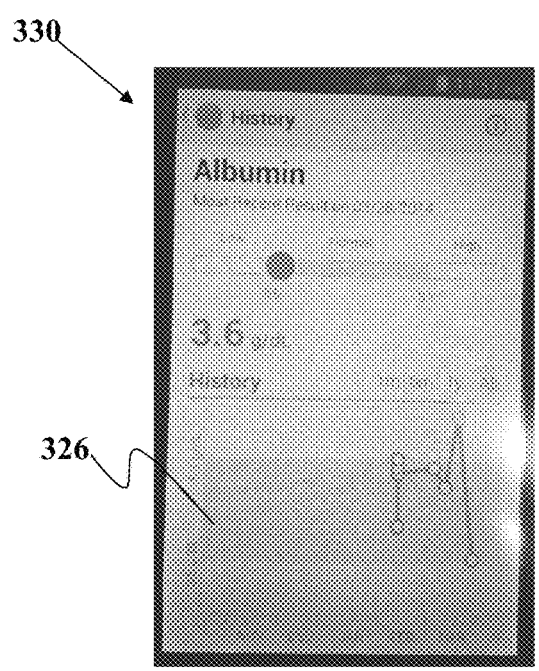

Referring now to FIG. 4G, a screen page 330 which shows a history of test results for that specific assay. By way of non-limiting example, FIG. 4G shows one region with the numeric value of the test result, a display of the data range, and a graph showing the history of results of the assay from current and previous testing event(s). This historical view of the results may be represented as a line graph, bar chart, or other visual representation to convey information to the user.

FIG. 4G shows that in the history, there was at least one out-of-range measurements as noted by the different colored data marker and data line extending outside a normal result reading range shown by the colored band 326.

Figure 4H:
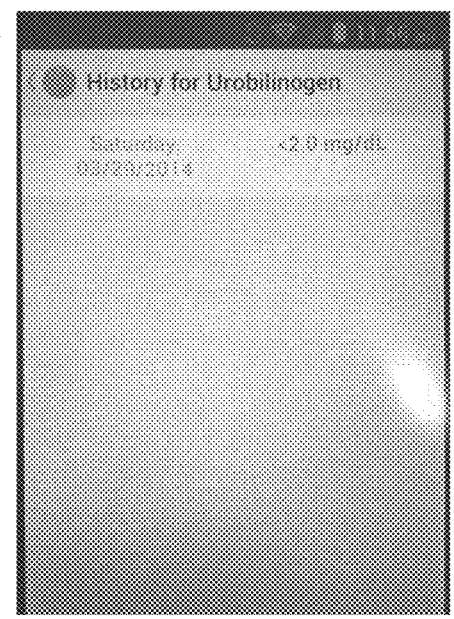

Referring now to FIG. 4H, a screen page 340 is shown of text showing test results displayed in text and color.

Figure 5A:
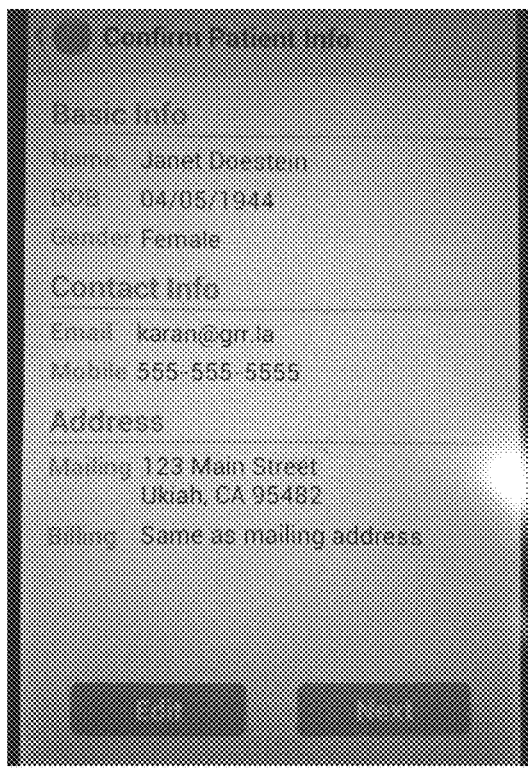
FIGS. 5A to 5C show various user interfaces according to at least some embodiments described herein.
Figure 5B:
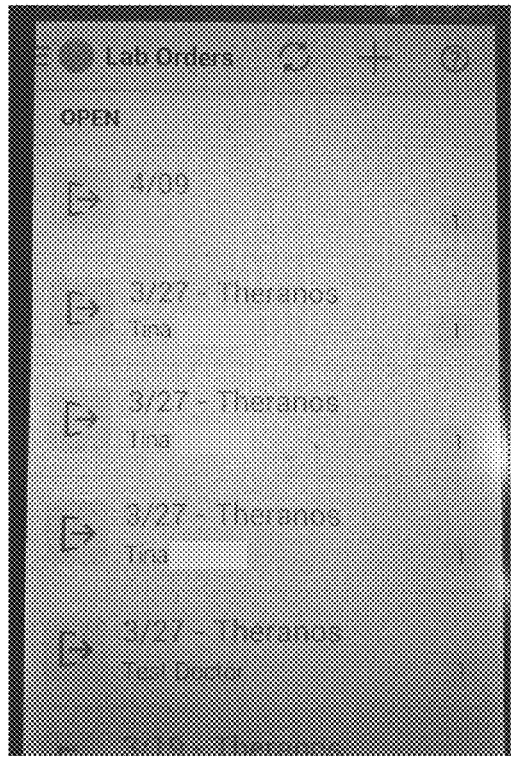
Figure 5C:
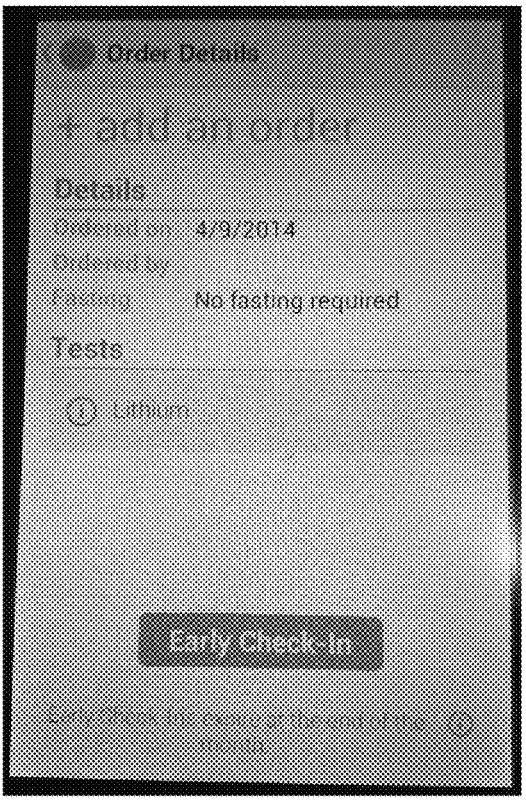

Referring now to FIGS. 5A to 5C, still other features will now be described. FIG. 5A shows a screen page wherein a user can confirm patient information. This may be information about the user. Optionally, the user may be entering information about another person on the user's account, such as but not limited to a dependent, spouse, or the like.

Referring now to FIG. 5B, one embodiment of a screen page is shown of lab orders listed by date of the laboratory test and with the patient name for the test associated therewith.

Referring now to FIG. 5C, one embodiment of a screen page is shown of lab order details is shown, including an option to add a test order. Details of the upcoming laboratory test may include details regarding the test such as but not limited to test prerequisites such as whether the subject should be fasting or not. As seen in FIG. 5C, there may also be an early check-in option available by selecting that option on the screen page.

Figure 6A:
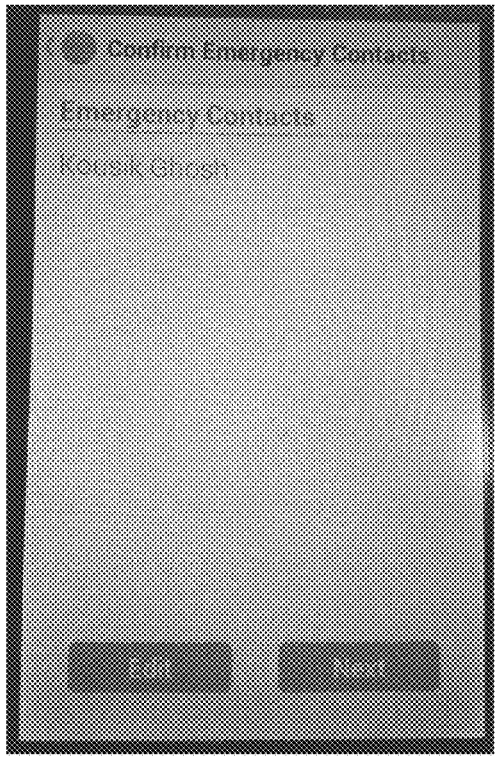
FIGS. 6A to 8B show various user interfaces and/or workflows according to at least some embodiments described herein.

Referring now to FIGS. 6A to 6D, still other features will now be described. Although not limited to the following, these screen pages are typically displayed to the user during the account setup process. It should be understood, of course, that embodiments may be configured wherein these screen pages are accessible to the user through account settings options that can be accessed even after initial account setup. FIG. 6A shows a screen page wherein a user is shown their emergency contacts and has the option to edit such contacts. Optionally, some embodiments may also include the option to add one or more emergency contacts. This may optionally lead to other screens that allow for input of this information.

Figure 6B:
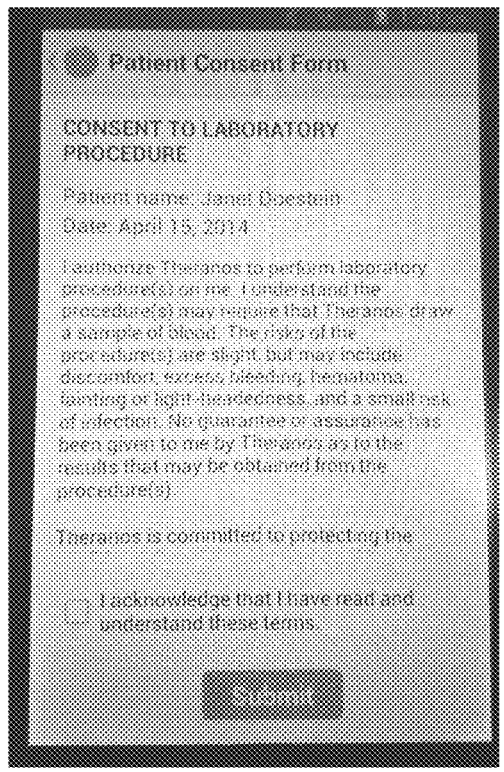

Referring now to FIG. 6B, another screen page that may appear during account setup is a patient consent form screen page. This screen page may appear even if the user may have previously setup an account using a different method (online, desktop, at a retail site, etc. . . . ) but this is the first time the user has setup an account on a mobile computing device. As seem in FIG. 6B, this form may include a required acknowledgement from the user in terms of checkbox, dialog box, or other item that must be clicked or require some other action from the user before the user can go on with account setup. Optionally, some embodiments may not make such selection a mandatory requirement. The action may be used to signify user acknowledgement of the terms and conditions, privacy settings, or other legal language.

Figure 6C:
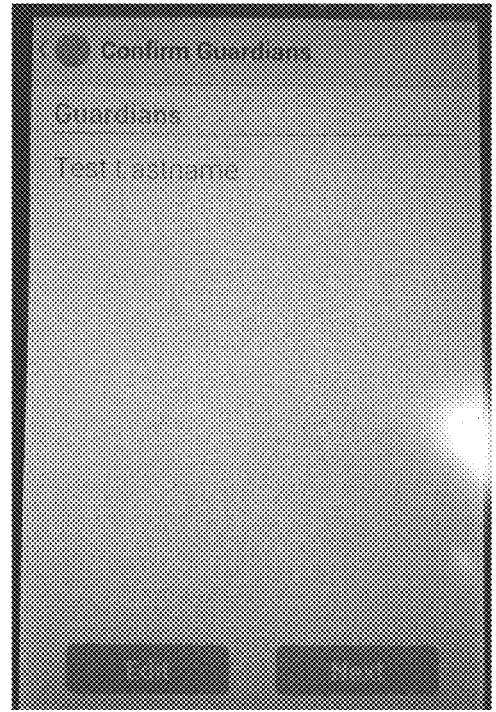

Referring now to FIG. 6C, another screen page that may appear during account setup is a patient guardian(s) screen page. This screen page may be optional depending on the age of the user, as this page is typically associated with users who are considered minors or those who have legal guardians because of other reasons.

Figure 6D:
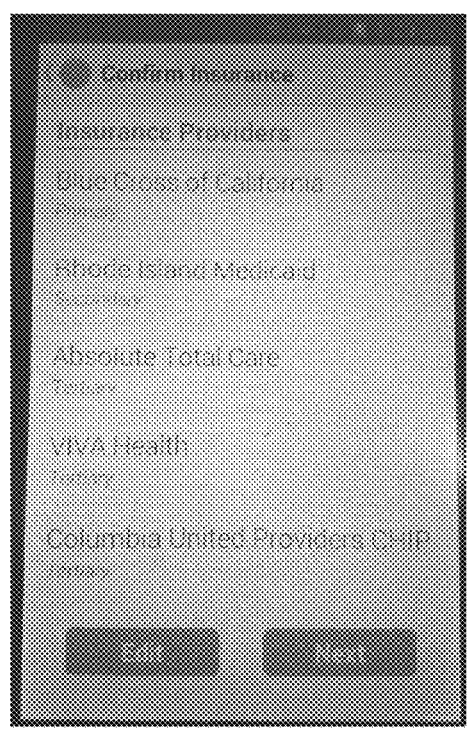

Referring now to FIG. 6D, another screen page that may appear during account setup is a medical insurance screen page. FIG. 6D shows that this embodiment a screen page is displayed wherein a user is shown their medical insurance information associated with the user and has the option to edit such insurance information. Optionally, some embodiments may also include the option to add one or more other insurances. Optionally, if this is an initial account setup, there may be no insurance information on-file and the user may be prompted to add at least one insurance into their account. If the user has no insurance, there is an option to note in the system that there is no insurance associated with the account. As seen in FIG. 6D, there may be a further option to designate the order for processing the insurance such as whether the insurance is primary, secondary, tertiary, or the like.

Figure 7A:
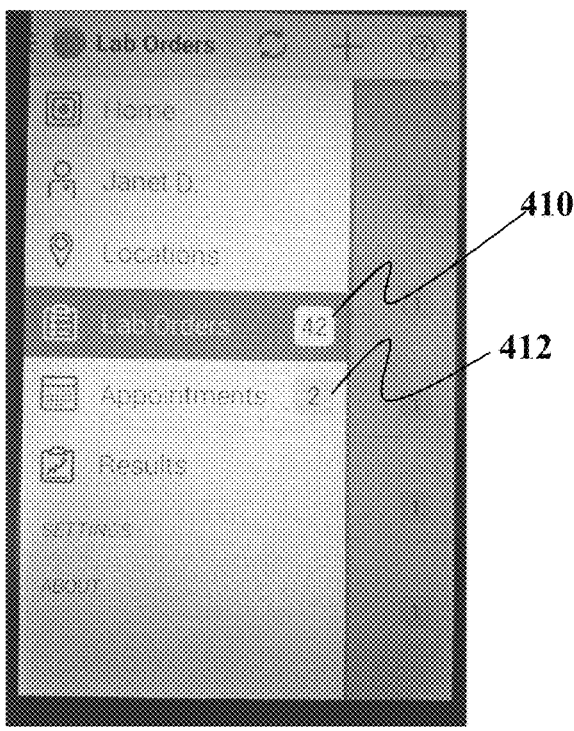

Referring now to FIGS. 7A to 8B, still other features will now be described. FIGS. 7A to 8B shows one embodiment of a workflow to setup an appointment at a specific patient service center location. As seen in FIG. 7A, there may be notification "badge" or other indicator 410 to show the number of lab orders pending. Optionally, another indicator 412 shows the number of appointments pending. It should be understood that the other categories listed such as but not limited to "results", "locations", or others may also include a notification "badge" or other indicator to show if there is an unread message, active/pending event, or other activity in that category.

Also as seen in FIG. 7A, one option for beginning the scheduling workflow for a new appointment comprises selecting the "lab orders" option from a dashboard, slide-out menu, or other display of the application. Of course, it should be understood that the application may have other options to reaching a create-an-appointment screen page. Optionally, a user may be able to arrive at the screen page of FIG. 7B by selecting the "make appointment" icon from the homepage.

Figure 7B:
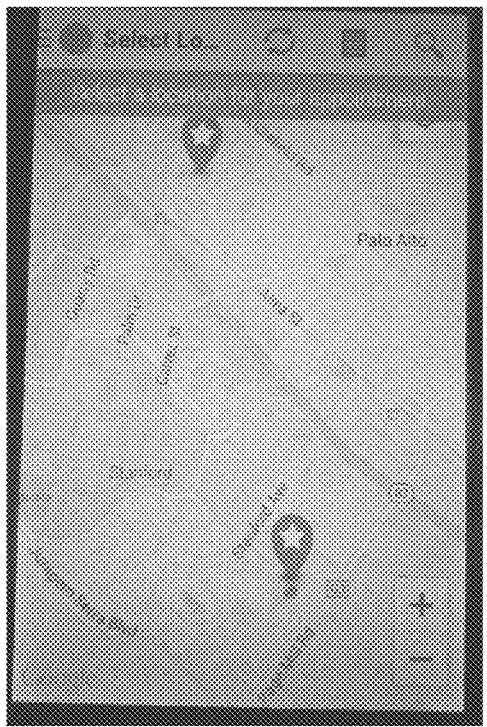

As seen in FIG. 7B, this embodiment of the workflow starts with the user selecting a location for the user's appointment. In one non-limiting example, this selection may be aided by presenting, graphically, textually, a combination of at least two, a combination of two or more of the foregoing, or by some other technique, patient service center location(s) near the user's location. This may be based on user location information that the user has opted to share with the application. Optionally, the user can manually enter the zip code, address, city, GPS coordinates, or other location identifier that the user may use to provide the location near which the user would like to schedule an appointment. Again, based on this information, the patient service center location(s) near that location may be presented graphically, textually, a combination of both, or by some other technique. The number of locations to be displayed may only show locations within a certain distance for the set locations. Optionally, some embodiments may be configured to display at least two locations to the user, regardless of the distance required for the user to travel to display the at least two locations.

Figure 7C:
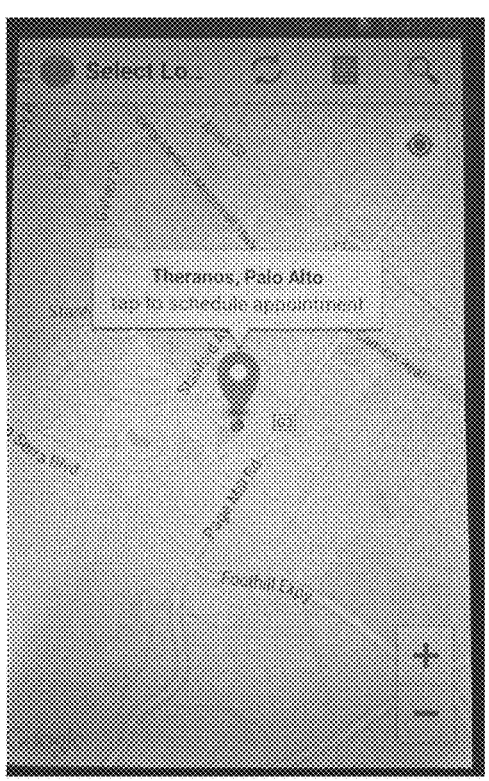

Referring now to FIG. 7C, it should be understood that some embodiments may optionally display the following screen page after a user has selected the patient service center for the appointment. In this non-limiting example, the screen page of FIG. 7C shows that the location selected will include a "tap to schedule appointment" display so that the user will confirm the location selection before moving onto the next screen page. Optionally, other selection methods such as a drop-down menu or the like can be used for selecting a location for appointment scheduling.

Figure 8A:
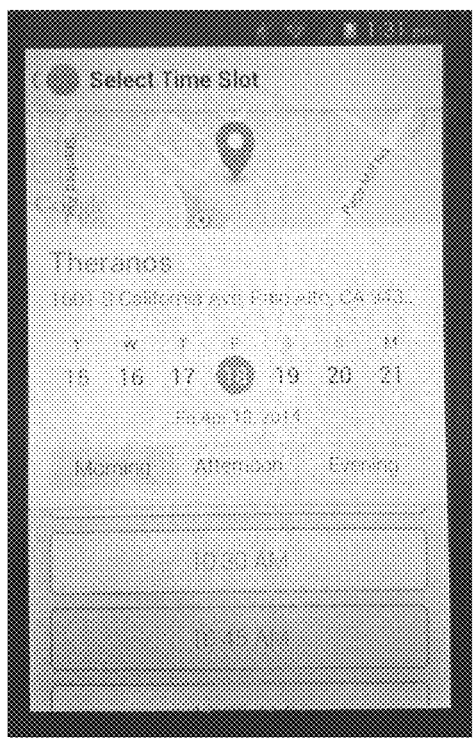

Referring now to FIG. 8A, a further feature may include a "select time slot" option for the appointment. This selection of time slot may optionally be the workflow after an appointment location is selected. Optionally, some embodiments may initially allow the user to select the time they would like for their appointment and then display the locations that have that time slot available. Optionally, some embodiments may display locations which may not have the exact time slot, but have time slots in a certain time period before and/or after desired time slot. Optionally, another embodiment can present a calendar (week, work week, whole week, monthly, etc. . . . ) that shows the number of appointments during the whole day, in the morning, in the afternoon, in the evening, or other time segmentation for the appointments at the available location(s).

Optionally, FIG. 8A shows that in this non-limiting example, the screen page may display at least a portion of a map showing the location of the patient service center on the map, text stating the facility name and address of the patient service center, a partial calendar graphically showing the date selected for the appointment, and text stating the date of the appointment. Optionally, one embodiment of the screen page may further include options for selecting the time of the appointment on the selected day, such as but not limited to a general time slot refinement option (morning, afternoon, evening) and specific time slots for select times. As seen in FIG. 8A, the specific time options may be presented as "tiles" listing the times or they may be a "slot machine" type display for setting hour, minute, and/or AM/PM.

Figure 8B:
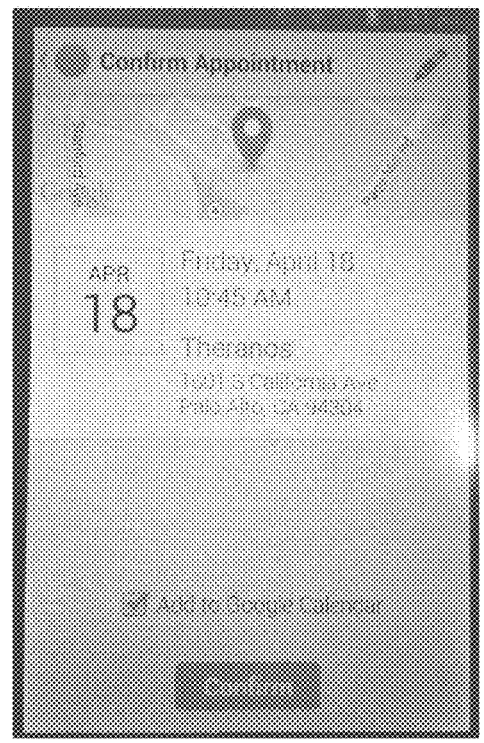

Referring now to FIG. 8B, once the desired appointment time is selected, in this non-limiting example, a confirmation screen page is displayed as shown in FIG. 8B. In this non-limiting example, again a map insert is shown with a marker thereon for the location of the selected patient service center for the appointment. In this non-limiting example, a banner is shown with a graphical calendar month/day displayed for the appointment day along with associated text for the day, month, day of the week, and time of the appointment. Optionally, the location and name of the selected patient service center for the appointment is also displayed. Optionally, there is also an option to include the appointment onto a calendaring service associated with the computing device. As seen in FIG. 8B, this may be set as a default to be opt-in with a check box or other selector to opt-out. Optionally, this may be reversed so that the opt-out is the default and opt-in for the calendar will require user action. Optionally, the calendaring option is not limited to only one option and other options for calendaring may be presented. Optionally, some embodiments of the application may allow for more than one calendaring system to be synchronized with this appointment time.

Figure 9A:
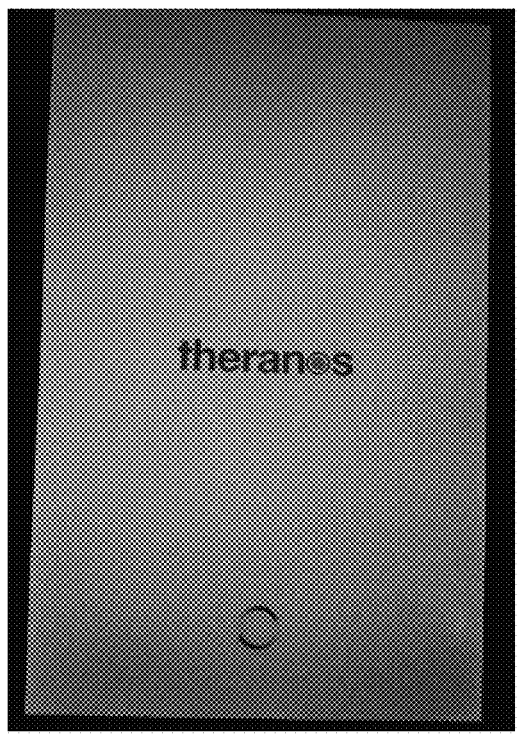
FIGS. 9A to 9D show a user unlock interface according to at least one embodiment herein.

Referring now to FIGS. 9A to 9D, a further feature associated with at least some embodiment will now be described. FIGS. 9A to 9D show at least some sequences associated with a screen-unlock feature that may be configured for use with embodiments herein. FIG. 9A shows an interim screen that may be displayed during application launch or other transition periods such as but not limited to when a user re-enters, re-opens, or otherwise transitions the application from a background status to an active status.

Figure 9B:
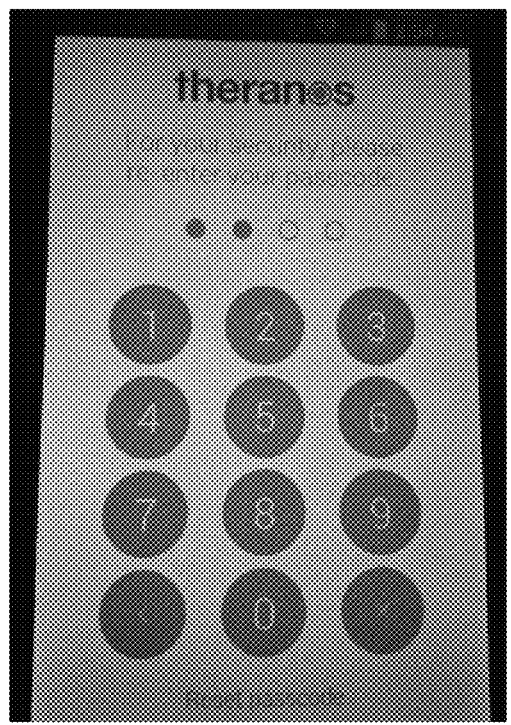
Figure 9C:
Figure 9D:

As seen in FIGS. 9B and 9C, once the screen-unlock page is displayed, the user is shown a "keypad" for entering an unlock code. As seen in FIG. 9B, there may be a visual guide showing the number digits, letters, or combinations for the unlock code. Progress indicators can be provided so that the user has feedback on their progress in entering the unlock code. FIG. 9C shows a screen page wherein three of the entries for the unlock code have been entered. FIG. 9D shows a screen page wherein all of the entries for the unlock code have been entered. Some embodiments may automatically unlock after the correct code is entered. Optionally, some embodiments may have the user press an additional key such as but not limited to an "enter" key, "return" key, "hash" key, or similar key to submit the code for unlock.

Figure 10A:
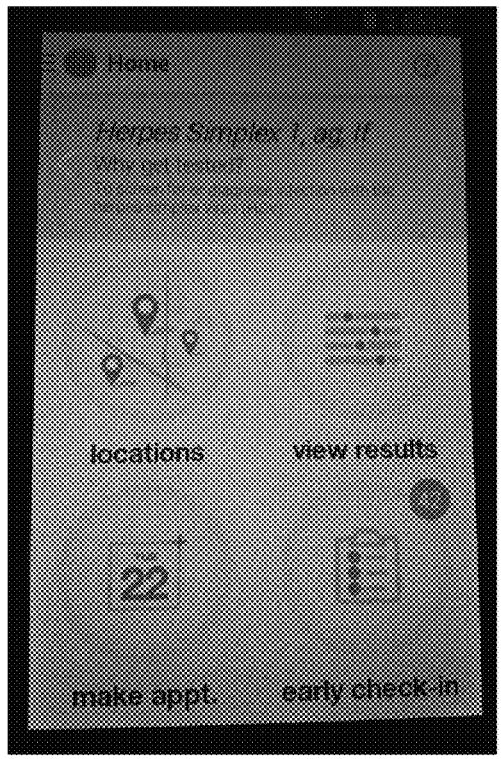
FIGS. 10A to 10D show various user interfaces for account setup according to at least some embodiments herein.

Referring now to FIGS. 10A to 10D, still further features associated with one or more embodiments of the application will now be described. FIG. 10A shows an embodiment wherein a banner on the screen page displays informational notices, which as seen in FIG. 10A, may relate to laboratory tests that may of interest to the user. FIG. 10A shows that this embodiment is displaying information regarding a herpes simplex virus test. The user is presented with an option to request more information.

Figure 10B:
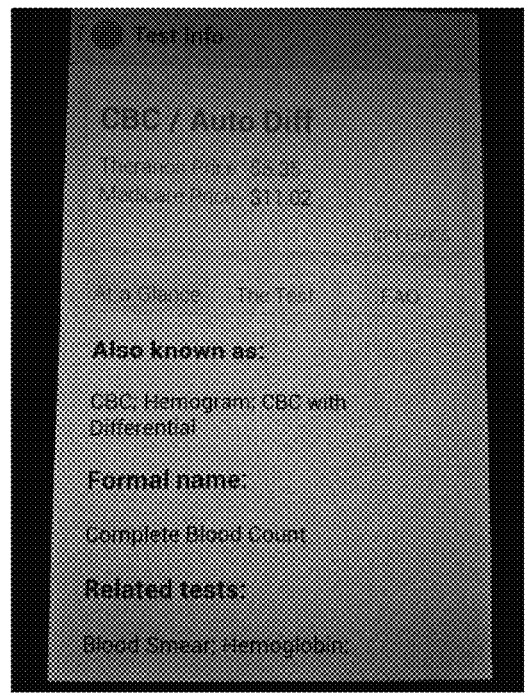

Referring now to FIG. 10B, if the user requests more information, the user will be provided information about the test. In one embodiment, this is done by providing a screen page that shows further information regarding the price and other information about the test. By way of non-limiting example, the "at a glance" tab is provided so that a user can have summary information about the test provided to them. In another embodiment, a tab may be provided to display more detailed information about the test. By way of non-limiting example, some embodiments may have an FAQ tab to provide answers to questions commonly asked by patients.

Figure 10C:
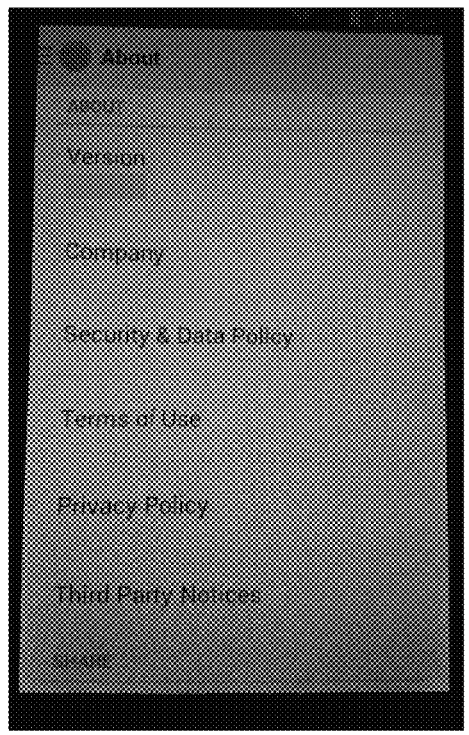
Figure 10D:
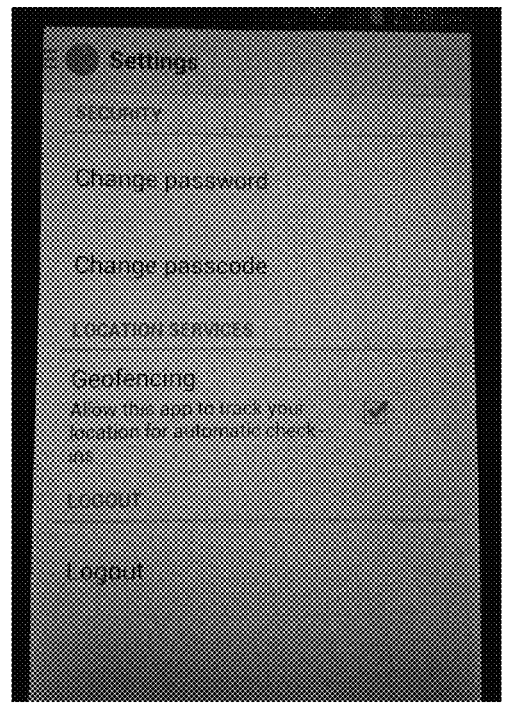
Figure 11A:
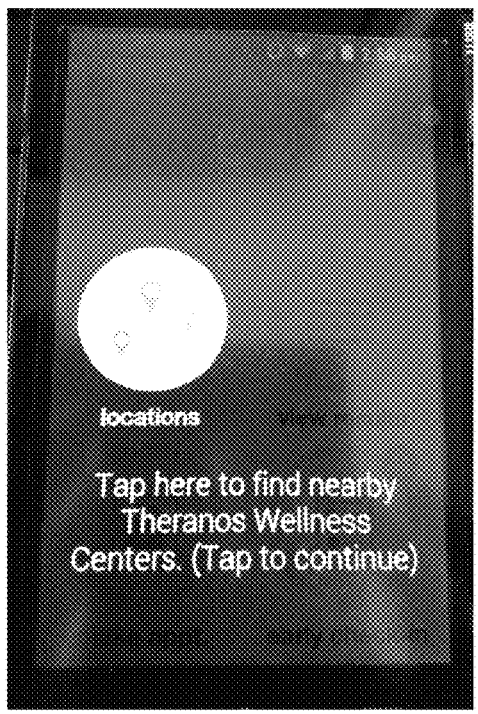
FIGS. 11A to 12B show various help screens according to at least some embodiments herein.
Figure 11B:
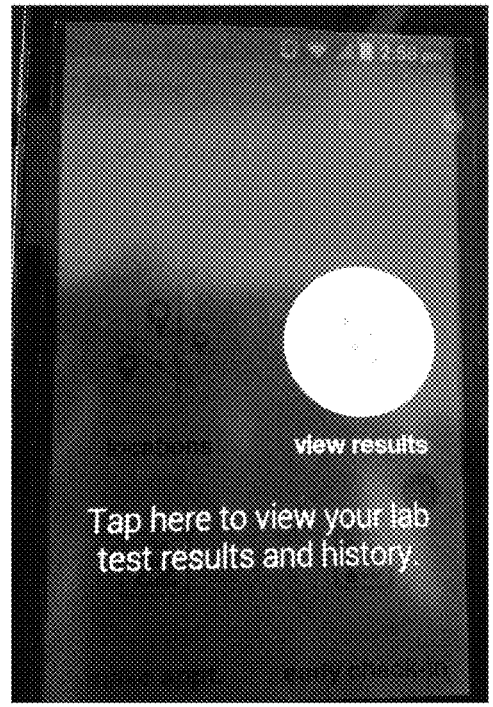
Figure 11C:
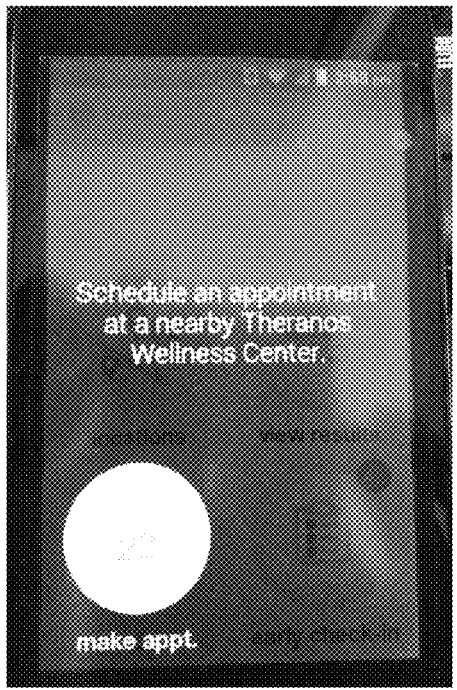
Figure 11D:
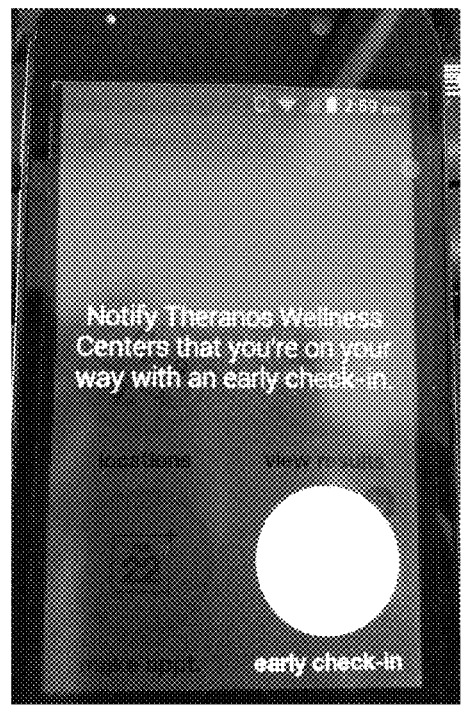
Figure 12A:
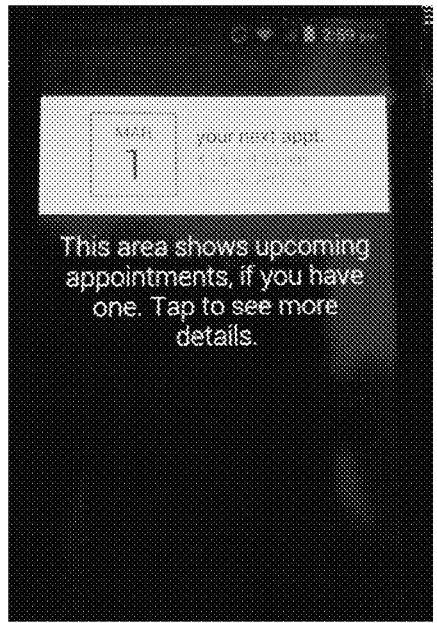
Figure 12B:
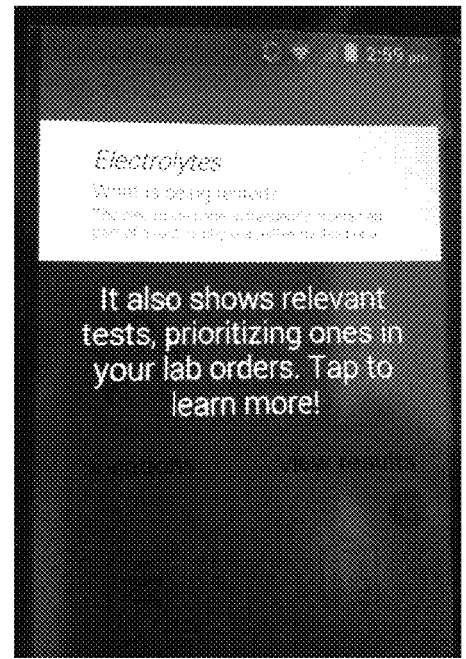

FIGS. 10C and 10D show still further embodiments of screen pages associated with the application. FIG. 10C show an "about" screen page with additional information regarding the application, including but not limited to use information such as a privacy policy or the like. FIG. 10D shows a "settings" screen page wherein the user can adjust security settings such as password or passcode. The present embodiment also provides an option to control location services such as but not limited to geofencing, which in the present embodiment may allow for automatic check-in for appointments based on location information provided by a subject's mobile computing device.

Referring now to FIGS. 11A to 12B, it should also be understood that some embodiments herein may also provide tutorial screen pages that provide information to the user regarding the use of certain features and/or to inform the user about the existence of selected features which can provide the user with a better understanding about the application.

Figure 13:
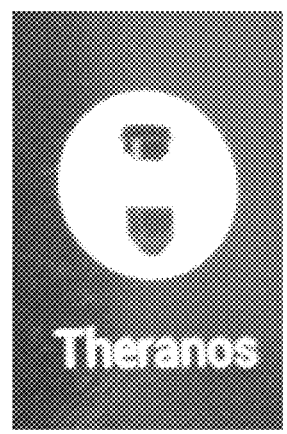
FIG. 13 shows one embodiment of an app icon as described in at least one embodiment herein.

Referring now to FIG. 13, a screenshot is provided of an icon that may be used to represent the application on a screen of the user's mobile device. Selecting this icon on the screen can be used to launch the application during initial use or selecting the icon can be used to re-enter the application after the user has temporarily exited the application.

Still further aspects of various user interface embodiments will now be described. In some embodiments, it should be understood that from one tab on the menu (in this example, the location tab), one can select the category to provide additional information. Herein the user can be presented with a list of nearby locations based on GPS location provided by the phone or other location information (such as but not limited to wifi based location or additional systems for providing location not based exclusively on GPS). On the listing page, contacting the map icon can also provide a map view of the locations from which details on that particular location can be displayed on the user interface.

In some embodiments, it should be understood that if one desires to locate locations not near the current location of the user, then there is an option to engage the search icon to enter other information such as but not limited to zip code, street, city, state, etc. . . . to provide a new list of locations based on the provided information.

In some embodiments, it should be understood that that there may be options to favorite or otherwise store preferred locations such that they can be retrieved by the device and/or marked to be shown as such.

Still further aspects of various user interface embodiments will now be described. This embodiment shows that selecting the "results" category allows the user to show a list of result including but not limited to unread results, past results, and/or dependent results. Optionally, the number displayed can indicate the number of results that may be out of the normal range. Optionally, the number itself, the background, and/or foreground colors can be selected to correspond to an urgency of response (yellow, red, etc. . . . ). In this embodiment, the results page can show the results summary of various panels, color indicated number or area for out-of-normal results, and/or comments from a medical professional. As seen in FIG. 5, if there are no out-of-normal results, no color indicator and/or number may be used to show that results were acceptable. Optionally, some embodiments may indicate visually by color (green or other positive-connotation color), shape, and/or text that the results were acceptable.

In some embodiments, it should be understood that on the detail page for the test results of a specific panel (in this example, the CBC panel), specific details of the test results are shown. For tests results where the output is a numeric value, the value and/or a position indicator of that value for results in an acceptable range can be shown. By way of non-limiting example, the data range of results can be normalized so that the normal "green" range is the same width and/or other dimension on the display. By normalizing the width of the normal "range" for test results, a user can visually access where their results are in one analyte or category in comparison to other results for other analyte(s) and/or categories. In this particular embodiment shown in FIG. 4E, a user can view the results and by viewing the results from the top to bottom or vice versa, can get a qualitative sense of where they stand in terms of their test results being in the normal range. By way of non-limiting example, results outside the range can be indicate by number, font size, font style, color and/or other indicator to show that they are not in the normal range. It should also be understood that although this example shows the results using horizontal bars, some embodiments may use vertical bars and/or other graphing techniques to display the results. Normalization of ranges can also be used in those other graphical presentations. Of course, it should be understood that display of results in a non-normalized manner is not excluded. Optionally, some may normalize ranges for a portion of the results and not all of them. It should also be understood that the ranges can be generic ranges, ranges based on the particular patient, this particular patient class, and/or some other selection criteria. It should be understood that some embodiments may use a mix of individual, class, and/or other criteria based ranges for the test results.

In some embodiments, it should be understood that for at least some embodiments, when new test results are received, a user can receive that notice in the dashboard and/or in the activity/update icon on the device status bar or other area where the device may indicate a new message or other activity has occurred. In some embodiments, the user can more quickly navigate directly to the test result details from the dashboard screen page, instead of having to show a listing of all test results and then selecting from that list.

It should be understood that for at least some embodiments, the user can also search the results based on variables such as text and/or other information in the test results. Optionally, the results can be filtered in real-time as the user enters the search query. Optionally, some embodiments may only show the results after the query is submitted by the user. Instead of text, some searches can be based on other criteria such as but not limited to only those results with out-of-range results, panic results, and/or other criteria which may be based on text entry, drop-down menu entry, check boxes, and/or other selection technique.

Still further aspects of various user interface embodiments will now be described. At least some embodiments may be able to allow a user to share full or partial results with another medical profession, which may be different from the medical profession or other entity that ordered the test. By way of non-limiting example, there may be an icon that is used to initiate the mailing of results to another party such as but not limited to a medical professional. Optionally, some embodiments may be configured such that the information can only be sent to another party that is a medical professional or otherwise authorized to receive a user's private health information. After sharing, there may be a process for confirming to the user that the information has been shared. Optionally, some embodiments may also include information (visual or otherwise) noting which results have been shared. As seen in FIG. 6B, text or other information can also be entered by the user to accompany the results. Optionally, the results can be sent directly to the other party or a link may be sent to the other party that will connect to display the actual results.

Still further aspects of various user interface embodiments will now be described. In some embodiments, it should be understood that various techniques for viewing anonymous testing results may be provided. In one embodiment, a user can see from the list of test results that one of them is for an anonymous test. A user can prompted to input a code, unlock pattern, other passkey, fingerprint, retinal scan, biomarker, or other unlock credential to present the test data. Optionally, it should be understood that when a biomarker or fingerprint is used, it does not reveal the user identity, only that the fingerprint, retinal scan, or biomarker matches the one used to initiate the anonymous testing. Once the results code or other unlock code is verified, the user is shown the page listing the laboratory panels for the anonymous testing. Selecting the one or more panels will then reveal the exact test results for the screen conditions. Optionally, once the results code or other unlock code is verified, the test results may be directly displayed, without having to view the test panel page. Optionally, some embodiments may have an entirely separate page for anonymous results which can only be displayed upon entry of user unlock credential which may be the same or different for unlock credentials for the underlying test. In this manner, the anonymous test results are not shown in the list of regular test results and thus does not raise suspicions that any anonymous testing has occurred if another party sees the test results listing page.

Optionally, some embodiments may prompt the user to query whether they want to import their anonymous testing results into the user's personal profile. Optionally, the user may continue to set (by default or opt-in) the anonymous test results such that they can only be viewed by entry of an unlock credential. In this manner, even importing the results into a user profile does not remove all security features for the results. Optionally, the user may select to remove one or more of the security features.

Still further aspects of various user interface embodiments will now be described. In some embodiments, it should be understood that from the test results page, one can delete the anonymous test results by selecting the edit option. Depending on user settings, one may still be prompted to enter information to unlock the anonymous testing results. In one embodiment, the deletion of results is permanent and not reversible. Optionally, some may be reversible for a set time period. Optionally, some may be reversible within a set time period and upon entry of unlock credentials. As seen in FIG. 8, deleted results will no longer appear on the results screen.

Creating Appointments

Although various features of the system have been described above, still further aspects of various user interface embodiments included in one or more of the various embodiments herein. One embodiment of user interfaces may allow a user to create an appointment for a laboratory test, based in part on a lab order that is already associated with the user. In some embodiments, it should be understood that a user can select to pay for the test at the patient service center where the sample will be drawn. Optionally, they may be charged for any payment, copayment, or other fee at the time the appointment is made. Of course, if it turns out that the subject fails to make the appointment, no, partial, or full refund may be processed.

In some embodiments, it should be understood that the user can be requested to acknowledge that they have read and understood the patient consent form. In some embodiments, the check box or other confirmation device for acknowledgement may only appear after the user has scrolled through the entire patient consent form. Optionally, some embodiments may have check box or other acknowledgement visible and selectable by the user from the outset, without requiring the user to scroll through the entire text portion of the patient consent form.

In this embodiment, the user can also select the location for performing the sample collection. Optionally, the list may include locations near the user's current location, locations near a location selected by the user, locations near a default location, and/or favorite or other preferred locations set by the user or based on location that the user has visited or used in the past. Optionally, once a location is selected, a time slot can also be presented for the user to select their preferred locations. Optionally, some embodiments may have the user select a time slot (or slots or time ranges) and then only present those locations that have availability. Optionally, the user may opt to view a calendar of open slots for a location or locations. This allows a user to review a variety of different factors and select a time slot based on multiple factors such as different day, time appointments are available, location, and/or other services available at that location. Optionally, some locations may only have certain types of testing or collection available and location presented can also limited to displaying only those that can perform tests noted in the lab order. Optionally, all locations can be presented but certain locations can be noted as ones with all testing or collection capability or only select capability.

Optionally, the payment option for the test may include "pay without insurance" if no insurance information has been entered into the system. Optionally, if insurance information is already entered, it can be selected as a choice for payment. Optionally, if the user desires to enter insurance information, they can do so on this screen by selection of an icon or other marker to take the user to that screen page.

Still further aspects of various user interface embodiments will now be described. Various user interfaces may include option(s) for the entry of insurance information, coupon codes, credit card information, pay at store, pay using a swiped credit card, and/or other payment services for use in payment for services to be provided. Optionally, the system may have a final cost breakdown showing payment information per line item and then requesting that the user confirm payment. After payment information is provided, a user may arrive at the order details page with updated appointment and payment information.

Still further aspects of various user interface embodiments will now be described. The various screenshots here show how a returning user with payment information already in the system can set-up appointments. After all information is provided, a user may arrive at the order details page with updated appointment and payment information.

Still further aspects of various user interface embodiments will now be described regarding accessing appointment details from the dashboard screen page. A user tapping on an appointment from the dashboard can bring up an appointment details page where the user can drill into associated lab orders or get directions.

In one non-limiting example, the user can access appointment details by selecting the lab order, where on the lab order details page, the user can select the lab appointment area. This brings the user to the appointment details screen.

In some embodiments, it should be understood that that user can edit an appointment, during the appointment scheduling process or after an appointment has been scheduled. Using at least one of the above techniques to arrive at the payment page, one can then change location, change time of the appointment or the like. Optionally, the changing of location can also present a new set of appointment times. Optionally, the changing of appointment times may present a new list of locations with availability for those appointment time(s). Some embodiments may allow for the selection of ranges of dates and/or times. Optionally, some embodiments may allow for calendar view of available slots at one or more locations, which can be useful if the user has a schedule that is not restricted to specific times.

In some embodiments, there can be options on the screen page for canceling an appointment. By way of non-limiting example, once a user is on the appointment details page, the options to edit the page includes canceling the appointment. Optionally, some embodiments may have the cancel appointment option on the dashboard as an icon or other item that is more directly accessible to the user. Once an appointment is canceled, the status of the lab order returns to the prior condition such as but not limited to "schedule appointment" or the like.

Still further aspects of various user interface embodiments will now be described. In some embodiments, it should be understood that one can on a single screen set the appointment for a plurality of laboratory orders. It should be understood that these orders can be from the same or different medical professionals. It should also be understood that these orders can be from the same or different medical organizations. In this manner, the sample collection for laboratory orders can be done at one location while the results can be for a plurality of different medical professionals/organizations. Optionally, the selection of multiple laboratory orders can be done by selecting checkboxes for each of the laboratory orders, or optionally, some embodiments are configured to default to select all open laboratory orders for that user, with an opt-out to un-select those orders that the user does not want to set for appointment.

Still further aspects of various user interface embodiments will now be described. In some embodiments, it should be understood that in some embodiments there is a short cut or reduced number of steps to reorder a completed or previous lab test. Optionally, in some embodiments, there is a short cut or reduced number of steps to reorder an expired lab test.

By way of non-limiting example, some embodiments may present an option to call the medical professional to discuss any concerns or issues.

Still further aspects of various user interface embodiments will now be described. In some embodiments, it should be understood that a user can self-order an anonymous test. In one non-limiting example, the test order page can show a plurality of tests that can be ordered under an anonymous basis. Optionally, a regular test menu can also be shown in some embodiments, wherein the "make results anonymous" option can anonymize those tests that have that option available. In this manner, the anonymous testing feature can be activated after tests are selected, instead of vice versa where the anonymous option is first selected and then a panel of anonymous tests is provided. Optionally, even when the anonymous test option is selected first, some embodiments herein can allow for the addition of one or more non-anonymous test after the desired test or tests are selected from the anonymous panel. Optionally, some embodiments allow for self-order of any tests in the test menu, based on location of the selected location, with or without a doctor's order. In this non-limiting example, the location of the user can be used to determine if a doctor's order is necessary. Optionally, the location of the appointment site is used to determine if a doctor's order is necessary based on state, federal, or local law for that location.

The anonymous testing may be shown with pricing of each test displayed to the user at the review order screen. Again, in this particular embodiment, the order details page shows the pricing of test(s). The user can schedule the appointment as part of the process related to creating and/or paying for the laboratory order.

Still further aspects of various user interface embodiments will now be described of how to edit user profile information. In one embodiment, a spinner selector can be invoked. A spinner may be similar to a drop down menu in that they do not block access to the rest of the screen. Others may use a dial or other selector.

Still further aspects of various user interface embodiments will now be described how it is possible to auto-populate information, such as but not limited to insurance provider information by capturing an image of the insurance provider card. In this non-limiting example, the user may select if the image will be of the front or the rear of the card. Optionally, some embodiments may not need the user to select which side of the card is being imaged; the system will extract information from the image and use as appropriate. In one non-limiting example, the user in at least some embodiments, can also set whether the insurance status is active or not. In some embodiments, it should be understood that there may be a user interface for removing insurance information for a user account.

Still further aspects of various user interface embodiments will now be described. wherein a user can also re-order the insurance priorities in the account such that primary, secondary, tertiary, and/or other designations can be associated with the various insurance and/or payment options. In some embodiments, it should be understood that one can set the insurance for one of the primary, secondary, tertiary, and/or other designated insurance to be inactive.

Still further aspects of various user interface embodiments will now be described. wherein at least one element on a screen page is provided where a user can set the dependents associated with the user account. In some embodiments, it should be understood that the user can manually enter the information.

Still further aspects of various user interface embodiments will now be described. wherein at least one element on a screen page can allow a user to set dependent information from the user's contact list. As seen in this embodiment, the user will be able to important information but will generally also be requested to supply other information that may not be included as part of the normal contact information (such as birthdate of the dependent, relationship to the primary member, if they have a different primary insurance, etc. . . . ).

Still further aspects of various user interface embodiments will now be described. wherein a user, for this embodiment, can edit the dependent information and/or edit or delete their relationship information. The information can be edited using the mobile device and/or can by synchronized with any changes made through other user devices accessing the same account, such as but not limited through changes on a website. Although the embodiments herein describe the user interface as through an application on a mobile device, it should be understood that for any of the user interfaces and/or workflows herein that the changes may be made on a website, such as but not limited to ones with specific domain suffixes like .me or the like. By way of example and not limitation, medical professionals may edit their profiles and information through websites such as those with an .md suffix.

Still further aspects of various user interface embodiments will now be described wherein a user, for this non-limiting example, can edit the payment information, particularly for non-insurance payment methods. It should be understood that security protocols for secure transmission of payment information can be used to protect the information that is being sent.

Still further aspects of various user interface embodiments will now be described wherein the user can also edit the payment information such as for credit card payment information. Optionally, the credit card information can also be deleted, as selected from a list of possible payment items.

Still further aspects of various user interface embodiments will now be described wherein for this embodiment, a user can change password or other security setting.

Still further aspects of various user interface embodiments will now be described wherein for this embodiment, a user can select the copyright print in the sidebar and by doing so can invoke a spinner that allows a user to read the privacy policy and/or the terms of use.

Still further aspects of various user interface embodiments will now be described wherein for this embodiment, the user is shown a login page wherein after the login process, the user is taken to a dashboard where the user is shown a health tracker or summary page of relevant health parameters, lab results, and/or lab orders.

Still further aspects of various user interface embodiments will now be described. FIGS. 11A-12B shows that for this embodiment, the user is provided a tutorial that can communicate values and/or features to the user. The user can also be shown a map of nearby testing locations.

Still further aspects of various user interface embodiments will now be described wherein for this embodiment, the user can sign-up for the service once they have acknowledged the various privacy forms, terms of use, and/or privacy policy. In one non-limiting example, all of these acknowledgements can occur prior the user even filling out the email address, password, name, birthday, and/or user name fields. Optionally, all acknowledgements can occur after collection of information, but prior to completing account setup. Optionally, some embodiments may have a portion of the acknowledgements before entry of sign-up information and a portion after sign-up. Optionally, some acknowledgements, such as the HIPAA form, may require more than one check-box or other acknowledgement. For any of the acknowledgements herein, it should be understood that some may be configured so that the acknowledgement box or other interface for receiving the user's acknowledgement may be configure to appear only after all of the text, graphics, and/or information to be acknowledged has been displayed to the user.

In one non-limiting example, a close-up view of one embodiment of a first-time user dashboard and sidebar is shown. Optionally, some embodiments may include a returning user dashboard and sidebar.

Optionally, one embodiment of a system for restoring a user password is shown. This embodiment uses a temporary password. Optionally, some embodiments can be provided that re-set the password by taking the user directly to a re-set password interface, without using an intermediate temporary password.

Optionally, one embodiment of an interface provides for logging out a user.

Still further aspects of various user interface embodiments will now be described wherein one or more embodiments may include one or more features for the uploading of information for paper laboratory or test orders into the system. In this non-limiting example, an image can be captured of the physical laboratory order and then the information extracted from that image. By way of example, the image capture can be achieved through a camera (front or rear facing) that is part of the device, through a scanner attached to the device, and/or through other image capture device.

It should be understood that the captured image may have imperfections associated with the skill of the user, the quality of the image capture device, and/or the condition of the physical condition of the original laboratory order. Some embodiments herein may use a mechanical device with a clear cover to hold the original flat. Optionally, the image can be processed through services similar to Instagram, ImageMagick, Adobe Acrobat Pro, or the like to condition the image to be in a state that allows for accurate data capture of information on the laboratory order. By way of non-limiting example, creases or other fold lines in the laboratory order can detected and then deleted or minimized so as not to interfere with data capture of information on the laboratory order. Optionally, some embodiments may use image processing to find and remove a long line, more than 1 pixel wide or remove all horizontal or vertical black lines that are at least 30 pixels long. Optionally, the image can be compared to known forms of laboratory orders, which can then be used to decipher text that may be unclear. The type of known form can be selected based on an initial image capture that may include the name of the referring physician or laboratory and/or any laboratory form identification number. The image processing can occur on the user's device, in a server, and/or on both.

In one non-limiting example, images of the laboratory order can loaded from a user's album of photos on the user's. Optionally, it can be loaded from an on-line album of photos that are not resident on the user's device.

Various techniques and user interfaces for updating a user's profile information are shown.

One embodiment will now be described for uploading insurance information and/or deleting insurance information from a category view of a plurality of insurance options. The insurance may optionally be verified by connection to a back-end processing server that has insurance information that confirms that the insurance information a user enters is up-to-date and that the insurance coverage is verified as valid.

Non-limiting examples of using the drag-and-drop feature to reorder the insurance priorities is shown. Optionally, one embodiment allows a user to set the insurance provider to inactive. This embodiment can also ask the user about the reason for the change.

Techniques for how dependent information may be entered and/or edited. This can be done using techniques as previously described herein.

In one non-limiting embodiment, a screen page is provided so that emergency contact information can be entered into a user's profile. Optionally, a user can import an emergency contact from the user's contact information on the device or on a server. The user can also add certain information such as birthdate, contact priority, relationship to the user, or the like. Some embodiments can create contact priorities based on the stated relationship to the user.

Still further aspects of various user interface embodiments will now be described. The user can add a doctor to the information for the user account. The doctor can be further selected from a "find a specialist" button to locate the type of specialist, wherein the result list can be sorted by distance from current location, alphabetically, or other criteria. Optionally, a user can edit a doctor's profile and/or remove it from the list.

User interfaces may have at least one webpage for adding and/or editing credit card information to the user account.

In one non-limiting example, a user interface is configured for adding and/or editing a medical condition associated with the user. In this non-limiting example, when a condition is added to a user profile such as their medical history, then a user can also enter information about a doctor who diagnosed the condition. Optionally, a user can also use this to add a condition this is currently symptomatic and perhaps not officially diagnosed. This can be selected, in one option, from the date where the user could not that this a current condition and the doctor which the user selected can be used to confirm this diagnosis. In one non-limiting example, a user can opt to have the system schedule an appointment with the doctor or optionally, have a message sent to the doctor about the condition, at which point the doctor or someone working with or associated with the doctor, can contact the user to follow-up on that condition.

In one non-limiting example, user interfaces/workflows are provided for adding and/or editing a medical condition associated with the user. This non-limiting example shows that user may first initiate the information input by selecting the doctor and is not limited to first selecting the condition. Thus, the sequence in which the information is input is not limited to order presented on the new condition user interface screen.

In one non-limiting example, user interfaces/workflows are configured for importing doctor or other medical professional information from contact list that the user has already created for other purposes. Optionally, even after import, the user may be requested to add additional information about the doctor. Optionally, the system can also auto populate some of this information by correlating the doctor's name and/or other identifier information to external or other databases to fill-in information that the user may not have provided. Some embodiments may prompt the user to confirm that the auto filled information is accurate or acceptable to the user before saving it to the user account.

One non-limiting example of user interfaces/workflows may include one or more features for adding "places" to the user account. These places can be, but are not limited to, places that are patient service centers that can collect samples for use with the testing associated with the system. The "my places" tab can save favorite or other locations that the user desires to have associated with their account. The "my places" tab can provide locations where the user has previously tested or where the user may prefer to go for testing. "My places" may be included in the default list of locations when results are pulled up for open appointment times, nearby locations, etc. . . . . They may be included as part of the list in a non-preferred manner, or preferentially listed at the top or other location in the listing. Optionally, some embodiments may use visual cues to highlight the locations which are part of the "my places".

Some embodiments may provide user interfaces/workflows for managing an appoint expiration alert. Optionally, some embodiments may provide user interfaces/workflows for managing a user's password. Optionally, some embodiments may provide user interfaces/workflows for obtaining user feedback on the application. Optionally, some embodiments may provide user interfaces/workflows for reviewing privacy policy and/or terms of use.

Non-limiting examples of user interfaces/workflows for user login screens may include information reminding users about conveniences or advantages of the present system, such as but not limited to the small size of the collected sample, slogans regarding advantages, visuals regarding the sample collected, lists of benefits, or the other reminders. Optionally, some embodiments can provide maps showing nearby test locations on the login screen.

Optionally, non-limiting examples of user interfaces/workflows for user login screens are shown.

Non-limiting examples of user interfaces/workflows for user login screens may comprise a login screen for the user where a password is required along with an associated username or email address. Optionally, a login screen may comprise or lead to a setup screen where a user can enter a PIN for locking or unlocking the program.

Non-limiting examples of user interfaces/workflows for user lab orders may comprise a green icon can be used to denote where a user can select different actions to bring-up a menu, dashboard, or the like. In one embodiment, the panel details may include results that are plotted along an acceptable range. Additional panel details can also be provided on the same or different screen. In one non-limiting example, the panel details and results are shown on the same page.

Non-limiting examples of user interfaces/workflows for ordering tests may include at least one screen page feature wherein a user selects the state in which the user plans to have the test conducted. Optionally, some embodiments may have the system configured such that a default location is entered into the test order interface and the user can opt to change it. Optionally, the default location can be input based on the user location based on GPS, IP, and/or other location information. Once the test state is selected, a menu of available tests can be displayed, from which the user can select the desired test(s). Optionally, pricing for the tests can also be display. It should be understood that in some embodiments, the pricing is shown for an un-subsidized and/or non-insurance covered user. Optionally, the pricing may include an additional column and/or other display option showing pricing based on default insurance coverage, some default pricing based on different insurance company, and/or based on insurance (primary, secondary, or otherwise) that the user has input into their profile. Optionally, the pricing based on insurance which the user may not have can be used to suggest to the user that certain insurance coverage may be beneficial to them. By way of non-limiting example, there may also be a link or click if the user desires to find out more about the sign-up, pricing, and/or cost for health insurance. This can result in a browser or other software application being opened that brings the user to a different user interface that has more information about the potential insurance coverage or other product that can be interest to the user.

Still further aspects of various user interface embodiments will now be described wherein a user can confirm the test order which may or may not also include the pricing. It should be understood that for those with insurance coverage, the pricing may be reduced to a single co-pay payment that would be the amount, assuming that insurance coverage for that test is or can be verified. Some embodiments may optionally also display a second dollar amount that would be the charge if the user's insurance authorization is not approved. A user may optionally be requested to confirm their order more than once, such as but not limited to clicking two check boxes or other confirmation interface, thus confirming that the authorize payment for either the insurance covered and/or the non-insurance covered pricing. Optionally, some embodiments can perform the dual confirmation by using separate user interface screens or the like.

In one non-limiting example, user menu screen can also be shown on one portion of the screen. Although full screen coverage is not excluded, the menu screen can be a menu that covers only a portion of the entire screen, leaving other portions visible and/or shadowed.

In one non-limiting example, interfaces may be provided on one or more screen pages for basic information about the user, guardian details, contact details, search doctors, and/or other information about the user.

Medical Professional Using Application to Schedule Appointment

Optionally, some embodiments may have a doctor or other authorized medical professional create an appointment using the workflow herein, except instead of scheduling appointments for themselves, they have the authorized credential(s) to schedule the appointment for their patient.

In this non-limiting example, this version of the scheduling application, similar to the "administrator-level" permissions or other high-than-standard permissions, allows the professional to use versions of the application described herein to order, to schedule, or to order and schedule clinical laboratory test(s) for a patient. This high-than-standard permission(s) may, in some embodiments, have a different workflow. Some embodiments may add to the workflow by having menu(s) or additional screen page(s) for selecting, entering, or otherwise identifying the patient for which the medical professional is creating the order/appointment. As described herein, some embodiments may allow the professional to scan in a barcode using the camera on his or her mobile device, scan an ID of the patient (wherein the ID may be one not issued by the professional scanning the barcode, to take an image of the test order and have the information optically recognized (wherein image process can occur at the local site or at a remote site), or allowing the professional to select from a list of patients from a drop-down menus, pick lists, or other known or future techniques for presenting filtered data sets for further filtering by user selection.

Multi-Source Data Integration

Data collection from multiple sources, such as but not limited to data from personal activity monitors, wifi enabled weight scales, and other monitoring devices can provide a significant amount of data with limited integration capabilities. The further category of data from clinical laboratory tests is yet another level of data that is without integration today. There may be some devices that a user can personally use to monitor level(s) of analyte(s), but those are typically analyte levels from waived devices.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the user interfaces herein are not limited to IOS or Android and that other operating systems are not excluded.

For some embodiments herein, as data is sent to the cloud, the metadata in the file may be corrupted or not provide desired information regarding when test was taken. Some embodiments herein may opt not to use any of the metadata associated with the data. Optionally, some embodiments may extract metadata at the device and include it as part of the data such as but not limited to a value of one or more the data fields that are transmitted, instead of residing in the background as metadata. Optionally, the harvesting of the metadata can occur in the cloud. It may continue to be part of the metadata of the file or it can be incorporated into one or more the data fields that are transmitted onward to the laboratory.

Some embodiments herein may include an opt-in and/or opt-out user interface page or question so that the user may select the privacy, clinical trial, and/or other participation in programs associated with the user and/or the test data.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes:

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not.

The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. A method for allowing a customer to order a clinical laboratory test with an application executing on an internet-enabled mobile device, where the internet-enabled mobile device comprises a processor, a memory coupled to the processor and a camera configured to capture an image that has at least a classification of disease code number encoded therein, the method comprising:

causing the processor to display an interface in the application executing on the internet-enabled mobile device, the interface for selection of a test order option;

receiving an input at the processor from the customer indicating, via the application, a selection of the test option; the application causing the processor to activate the internet-enabled mobile device's camera for scanning of a barcode; the application causing automatically or upon a user input, the camera to capture an image, displayed in the application, of the barcode indicating at least a test number; the application causing the processor to transmit from the application, over a network, to a server, data indicative of at least the test number so that the server can automatically validate the test number by verifying that the test number exists in a database of test numbers;

receiving information at the internet-enabled mobile device, over the network, at least a portion of which is to be displayed in an order review page of the application executing on the internet-enabled mobile device;

correcting the image captured by the camera using an image correction algorithm that removes defects in the image associated with fold lines or substantially linear type aberrations in the image;

comparing the corrected image to images of known laboratory forms to correct for data captured from the corrected image;

causing the processor to generate a display in the application including the at least the portion of received information in an order review page, wherein the information includes the test number and a test location where a sample is to be collected for the test; wherein the information to be displayed in the order review page includes a sample collection location and an option to change the sample collection location;

transmitting from the internet-enabled mobile device, in response to an action by the customer viewing the displayed order review page, to the server and via the network, a confirmation to schedule the test; and based on geographic location of a test site selected by the customer, causing the processor to display a further interface for a customer to self-order the laboratory test for the customer, without a physician's order, based on geographic location of test site that allows for such self-ordering,
wherein the displayed interface includes only a subset of tests available on a test menu for the selected test site.

2. The method of claim 1 further comprising,
allowing a user to order a test from within the application, the application causing:
automatically validating with one of the one or more processors the test number by verifying that the test number exists in a database of test numbers corresponding to previously filled test medications;
receiving over a network at the internet-enabled mobile device, test information when the test number was verified;
wherein the test information to be displayed in a second display includes a sample collection test location and an option to change the sample collection test location.

3. The method of claim 1 further comprising,
wherein a laboratory test menu of orderable tests varies based on geographic location.

4. The method of claim 1 wherein the bar code comprises a matrix barcode.

5. The method of claim 1 wherein the internet-enabled mobile device comprises a mobile phone.

6. The method of claim 1 wherein the internet-enabled mobile device has a touch sensitive display screen.

7. The method of claim 1 further comprising activating a global positioning system (GPS) device in the internet-enabled mobile device to provide a current position of the internet-enabled mobile device, wherein said location is used by the user to select the test site.

8. A system for receiving a customer laboratory order for a clinical laboratory test, the system comprising:
a communication network; one or more internet-enabled mobile devices, each internet-enabled mobile device having a processor, a memory coupled to the processor and a camera coupled to the processor and the memory; and one or more server computers communicatively coupled to the communication network and the one or more internet-enabled mobile devices; one of the one or more internet-enabled mobile devices having an application stored thereon; the application configured to cause the processor to display an interface in the application executing on the internet-enabled mobile device, the interface for selection of a test option; the application configured to receive an input at the processor from the customer indicating, via the application, a selection of the test option; the application configured to cause the processor to activate the internet-enabled mobile device's camera for scanning of a barcode; the application configured to cause, automatically or upon a user input, the camera to capture an image, displayed in the application, of the barcode indicating at least a test number, the test number corresponding to a test medication and a patient; the application configured to cause the processor to transmit from the application, over the communication network, to at least one of the one or more server computers, data indicative of at least the test number so that the server can automatically validate the test number by verifying that the test number exists in a database; the application configured to receive information at the internet-enabled mobile device, over the communication network, at least a portion of which is to be displayed in an order review page of the application executing on the internet-enabled mobile device; the application configured to cause the processor to generate a display in the application including the at least the portion of received information in an order review page, wherein the information includes the test number and a sample collection location; the application configured to transmit from the internet-enabled mobile device, in response to an action by the customer viewing the displayed order review page, to at least one of the one or more server computers and via the communication network, a test confirmation;
wherein based on geographic location of a test site selected by the customer, the internet-enable mobile device is configured to display an interface with test menu specific for that test site selected by the customer;
a device for correcting the image captured by the camera using an image correction algorithm that removes defects in the image associated with fold lines or substantially linear type aberrations in the image and comparing the corrected image to images of known laboratory forms to correct for data captured from the corrected image, wherein the displayed interface includes only a subset of tests available on a test menu for the selected test site.

9. The system of claim 8 wherein the barcode comprises a matrix barcode.

10. The system of claim 8 wherein the internet-enabled mobile device comprises a mobile phone.

11. The system of claim 8 wherein the internet-enabled mobile device has a touch sensitive display screen.

12. The system of claim 8 wherein the internet-enabled mobile device further comprises a global positioning system (GPS) device to provide a current position of the internet-enabled mobile device, wherein said location is used by the user to select the test site.

13. A method for allowing a customer to order a clinical laboratory test with an application executing on an internet-enabled mobile device, where the internet-enabled mobile device comprises a processor, a memory coupled to the processor and a camera configured to capture an image that has at least a classification of disease code number encoded therein, the method comprising:
causing the processor to display an interface in the application executing on the internet-enabled mobile device, the interface for selection of a test order option;
receiving an input at the processor from the customer indicating, via the application, a selection of the test option; the application causing the processor to activate the internet-enabled mobile device's camera for scanning of a barcode; the application causing automatically or upon a user input, the camera to capture an image, displayed in the application, of the barcode indicating at least a test number; the application causing the processor to transmit from the application, over a network, to a server, data indicative of at least the test number so that the server can automatically validate the test number by verifying that the test number exists in a database of test numbers;
receiving information at the internet-enabled mobile device, over the network, at least a portion of which is to be displayed in an order review page of the application executing on the internet-enabled mobile device;
correcting the image captured by the camera using an image correction algorithm that removes defects in the image associated with fold lines or substantially linear type aberrations in the image;

comparing the corrected image to images of known laboratory forms to correct for data captured from the corrected image;

causing the processor to generate a display in the application including the at least the portion of received information in an order review page, wherein the information includes the test number and a test location where a sample is to be collected for the test; wherein the information to be displayed in the order review page includes a sample collection location and an option to change the sample collection location;

transmitting from the internet-enabled mobile device, in response to an action by the customer viewing the displayed order review page, to the server and via the network, a confirmation to schedule the test; and based on geographic location of a test site selected by the customer, causing the processor to display a further interface for a customer to self-order the laboratory test for the customer, without a physician's order, based on geographic location of test site that allows for such self-ordering, wherein the displayed interface includes only a subset of tests available on a test menu for the selected test site;

wherein self-ordering is only activated based on geographic location of a selected test site that allows for such self-ordering.

14. The method of claim 13 wherein the bar code comprises a matrix barcode.

15. The method of claim 13 wherein the internet-enabled mobile device comprises a mobile phone.

16. The method of claim 13 wherein the internet-enabled mobile device has a touch sensitive display screen.

17. The method of claim 13 further comprising activating a global positioning system (GPS) device in the internet-enabled mobile device to provide a current position of the internet-enabled mobile device, wherein said current position is used by the user to select the test site.

* * * * *